United States Patent
Whyte et al.

(10) Patent No.: US 12,195,813 B2
(45) Date of Patent: Jan. 14, 2025

(54) AUTOMATED NESTED RECOMBINASE POLYMERASE AMPLIFICATION

(71) Applicant: ABBOTT DIAGNOSTICS SCARBOROUGH, INC., Scarborough, ME (US)

(72) Inventors: Murray John Whyte, Tillicoultry (GB); Niall A. Armes, Helions Bumpstead (GB); Olaf Piepenburg, Saffron Walden (GB); Catherine Jean Greenwood, Sawbridgeworth (GB); Oliver Nentwich, Cambridge (GB)

(73) Assignee: ABBOTT DIAGNOSTICS SCARBOROUGH, INC., Scarborough, ME (US)

( * ) Notice: Subject to any disclaimer, the term of this patent is extended or adjusted under 35 U.S.C. 154(b) by 0 days.

(21) Appl. No.: 16/081,941

(22) PCT Filed: Mar. 3, 2017

(86) PCT No.: PCT/US2017/020782
§ 371 (c)(1),
(2) Date: Sep. 3, 2018

(87) PCT Pub. No.: WO2017/152122
PCT Pub. Date: Sep. 8, 2017

(65) Prior Publication Data
US 2020/0232050 A1  Jul. 23, 2020

Related U.S. Application Data

(60) Provisional application No. 62/303,934, filed on Mar. 4, 2016.

(51) Int. Cl.
*C12Q 1/70* (2006.01)
*B01L 3/00* (2006.01)
*C12Q 1/6806* (2018.01)
*C12Q 1/686* (2018.01)
*G01N 27/416* (2006.01)

(52) U.S. Cl.
CPC ........... *C12Q 1/701* (2013.01); *C12Q 1/6806* (2013.01); *C12Q 1/686* (2013.01); *G01N 27/416* (2013.01); *B01L 3/5027* (2013.01)

(58) Field of Classification Search
CPC ................ C12Q 1/701; C12Q 1/6806
See application file for complete search history.

(56) References Cited

U.S. PATENT DOCUMENTS

| | | |
|---|---|---|
| 7,270,981 B2 | 9/2007 | Armes et al. |
| 7,399,590 B2 | 7/2008 | Piepenburg et al. |
| 7,435,561 B2 | 10/2008 | Piepenburg et al. |
| 7,666,598 B2 | 2/2010 | Piepenburg et al. |
| 8,062,850 B2 | 11/2011 | Piepenburg et al. |
| 8,071,308 B2 | 12/2011 | Piepenburg et al. |
| 8,580,507 B2 | 11/2013 | Piepenburg et al. |
| 8,637,253 B2 | 1/2014 | Piepenburg et al. |
| 8,697,363 B2 | 4/2014 | Mir et al. |
| 8,772,017 B2 | 7/2014 | Battrell et al. |
| 9,057,097 B2 | 6/2015 | Piepenburg et al. |
| 9,469,867 B2 | 10/2016 | Piepenburg et al. |
| 2003/0148310 A1* | 8/2003 | Sorge ............. C12Q 2537/1373 435/6.12 |
| 2009/0017453 A1 | 1/2009 | Maples et al. |
| 2009/0081670 A1 | 3/2009 | Maples et al. |
| 2009/0111089 A1 | 4/2009 | Lindstrom et al. |
| 2011/0053153 A1 | 3/2011 | Piepenburg et al. |
| 2012/0244534 A1 | 9/2012 | Ching et al. |
| 2012/0258456 A1* | 10/2012 | Armes ................. C12Q 1/6851 435/6.11 |
| 2019/0136300 A1* | 5/2019 | Bowler .................. C12P 19/34 |

FOREIGN PATENT DOCUMENTS

| | | |
|---|---|---|
| CN | 104195236 B | 8/2015 |
| JP | 2008500831 A | 1/2008 |
| JP | 2008517632 A | 5/2008 |
| JP | 2009529883 A | 8/2009 |

(Continued)

OTHER PUBLICATIONS

Van Elden (Simultaneous Detection of Influenza Viruses A and B Using Real-Time Quantitative Pcr, J Clin Immunol, 39(1): 196-200, 2001. (Year: 2001).*
Gencoglu, Electrochemical detection techniques in micro- and nanofluidic devices, Microfluid Nanofluid, 17: 781-807, 2014. (Year: 2014).*
Navarro, Real-time PCR detection chemistry, Clinica Chimica Acta, 439, 231-250, 2015. (Year: 2015).*

(Continued)

*Primary Examiner* — Carolyn L Greene
(74) *Attorney, Agent, or Firm* — Casimir Jones, S.C.; Thomas A. Isenbarger

(57) ABSTRACT

A flu assay system including a sample module, a microfluidic nucleic acid amplification device, and an analyzer to facilitate fully automated nested recombinase polymerase amplification (RPA) on a sample delivered to the nucleic acid amplification device via the sample module. The assay includes providing a sample to a microfluidic device, and amplifying a target polynucleotide sequence in the sample. Amplifying the target polynucleotide sequence includes performing a first round of amplification on the sample to yield a first amplification product, and performing a second round of amplification on the first amplification product to yield a second amplification product. The second amplification product includes a smaller sequence completely contained within the first amplification product produced during the first round of amplification.

20 Claims, 17 Drawing Sheets

Specification includes a Sequence Listing.

(56) References Cited

FOREIGN PATENT DOCUMENTS

| JP | 2014516512 A | 7/2014 |
|---|---|---|
| WO | 2006/099042 A2 | 9/2006 |
| WO | 2006/099042 A3 | 4/2007 |
| WO | 2010141940 | 12/2010 |
| WO | 2014/182847 A1 | 11/2014 |
| WO | 2015/015178 A2 | 2/2015 |
| WO | 2015/015178 A3 | 5/2015 |

OTHER PUBLICATIONS

Hocek, Nucleobase modification as redox DNA labelling for electrochemicaldetection, Chem. Soc. Rev., 2011, 40, 5802-5814, 14 pages.
Lin et al., Origins and evolution of the recA RAD51 gene family: Evidence for ancient gene duplicationand endosymbiotic gene transfer, PNAS USA 103:10328-10333, 2006, 6 pages.
International Search Report in corresponding International Application No. PCT/US2017/020782, mailed Sep. 8, 2017, 4 pages.
European Search Report of related EP17760946.8, mailed Sep. 9, 2019, 15 pages.
Extended European Search Report for 17760946.8, mailed Sep. 9, 2021, 18 pages.
Wang, F et al. Droplet-based microsystem for multi-step bioreactions. Biomed Microdevices. Jun. 2010; 12(3):533-41.
Tortajada-Genaro, L.A. et al. Isothermal solid-phase recombinase polymerase amplification on microfluidic digital versatile discs (DVDs). RSC Adv., 2015, 5, 29987-29995.
Santiago-Felipe, S. et al. One-pot isothermal DNA amplification—Hybridisation and detection by a disc-based method. 204, Dec. 1, 2014, 273-281.

\* cited by examiner

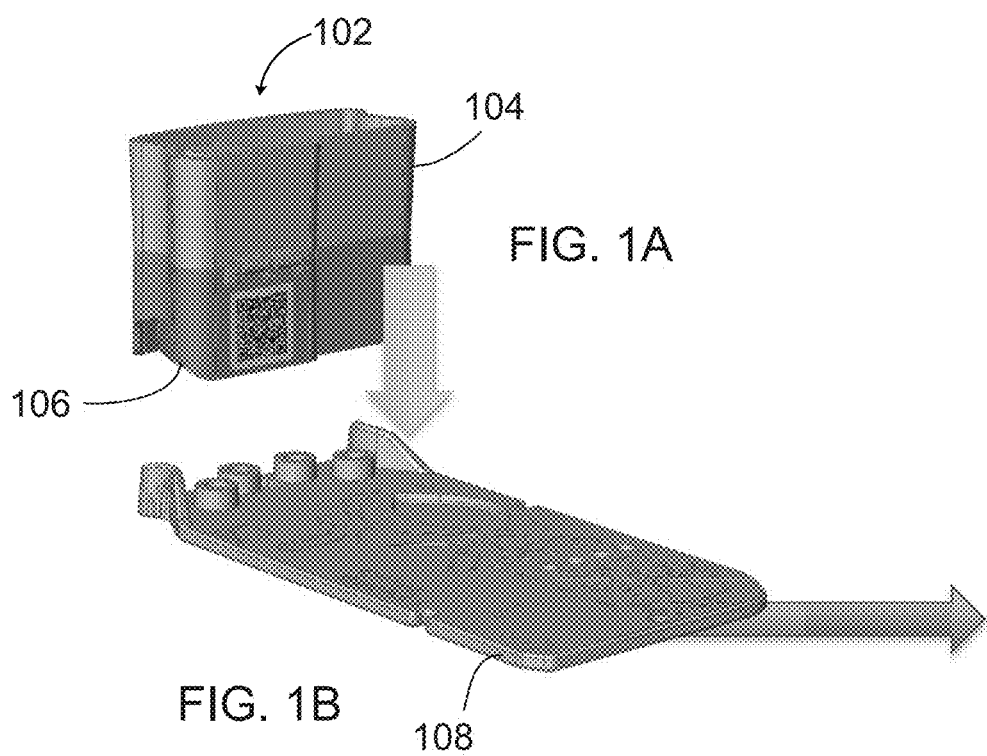
FIG. 1A
FIG. 1B
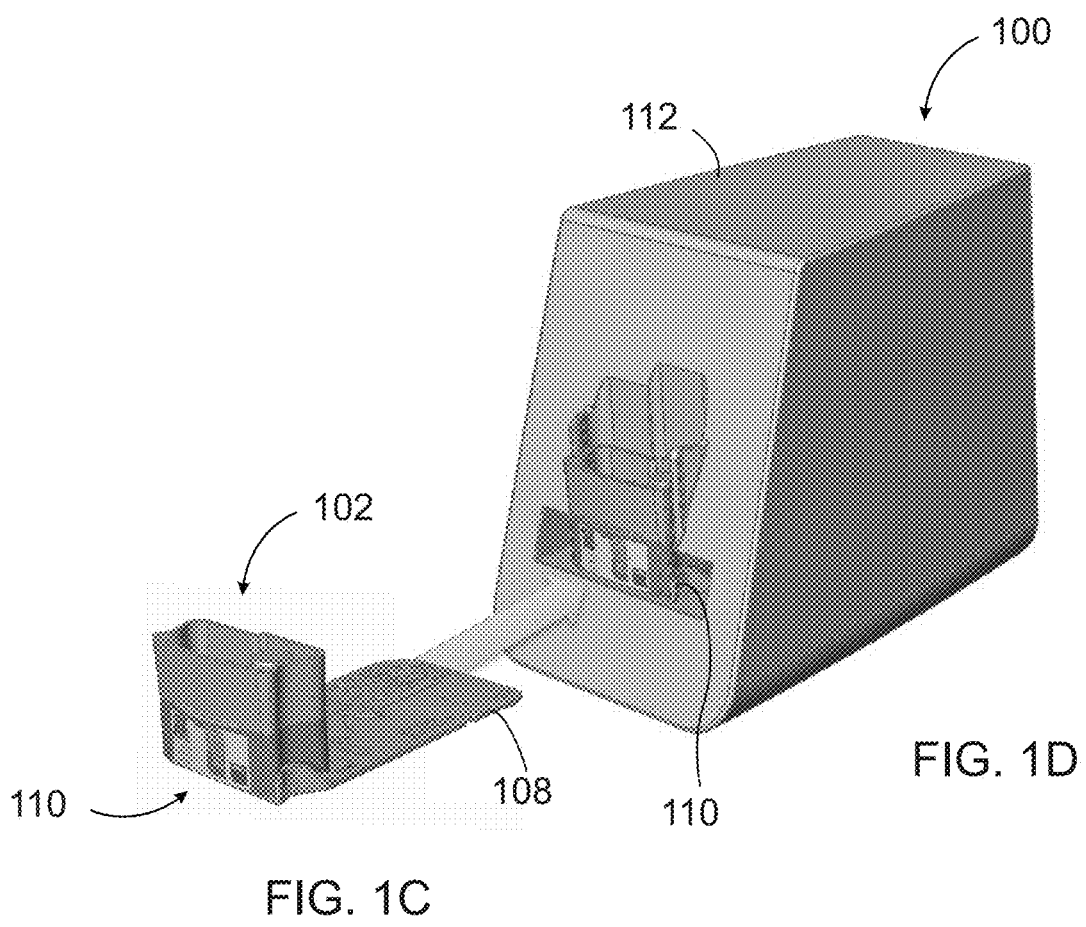
FIG. 1C
FIG. 1D

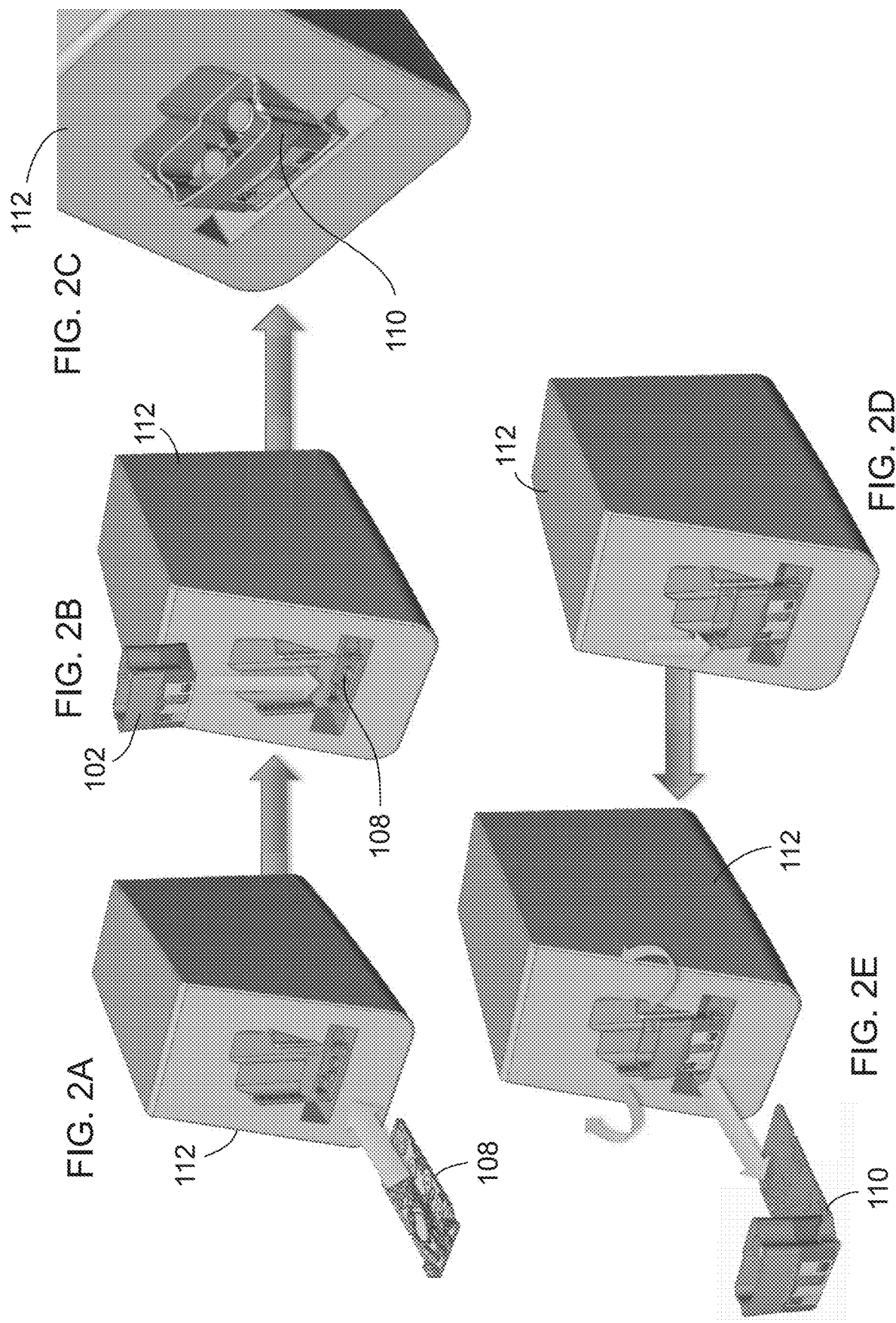

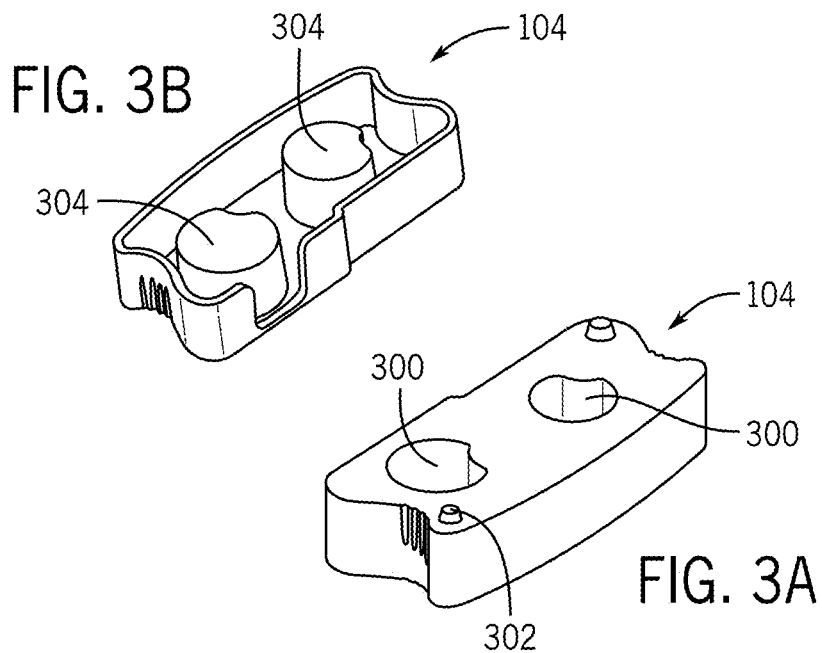
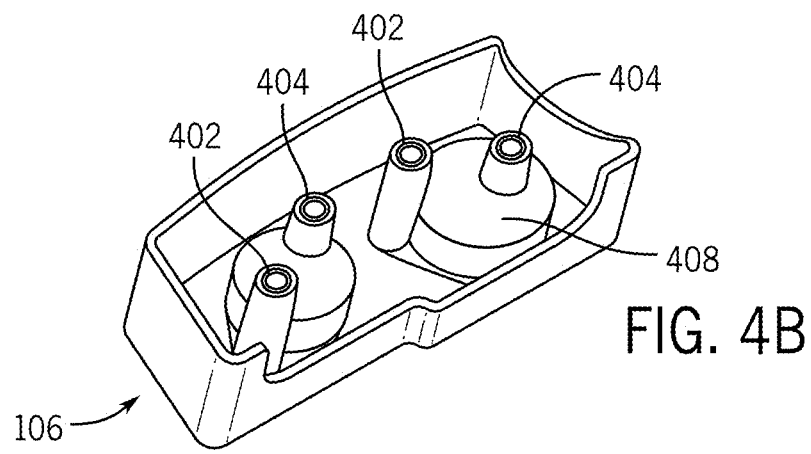
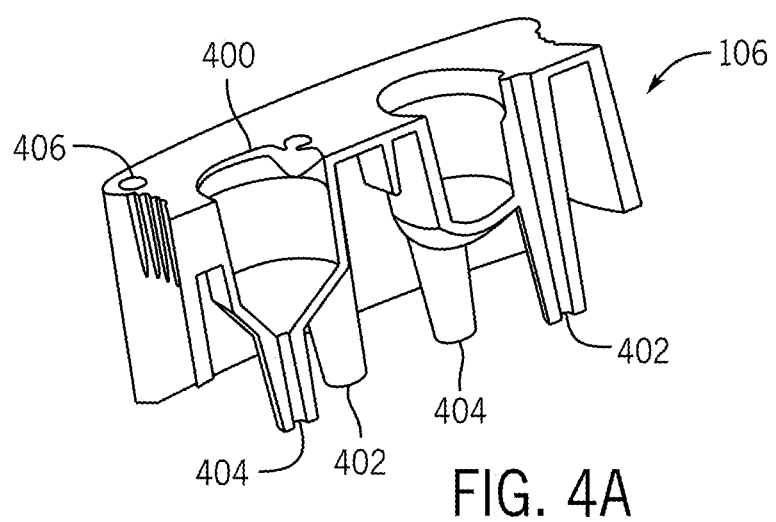

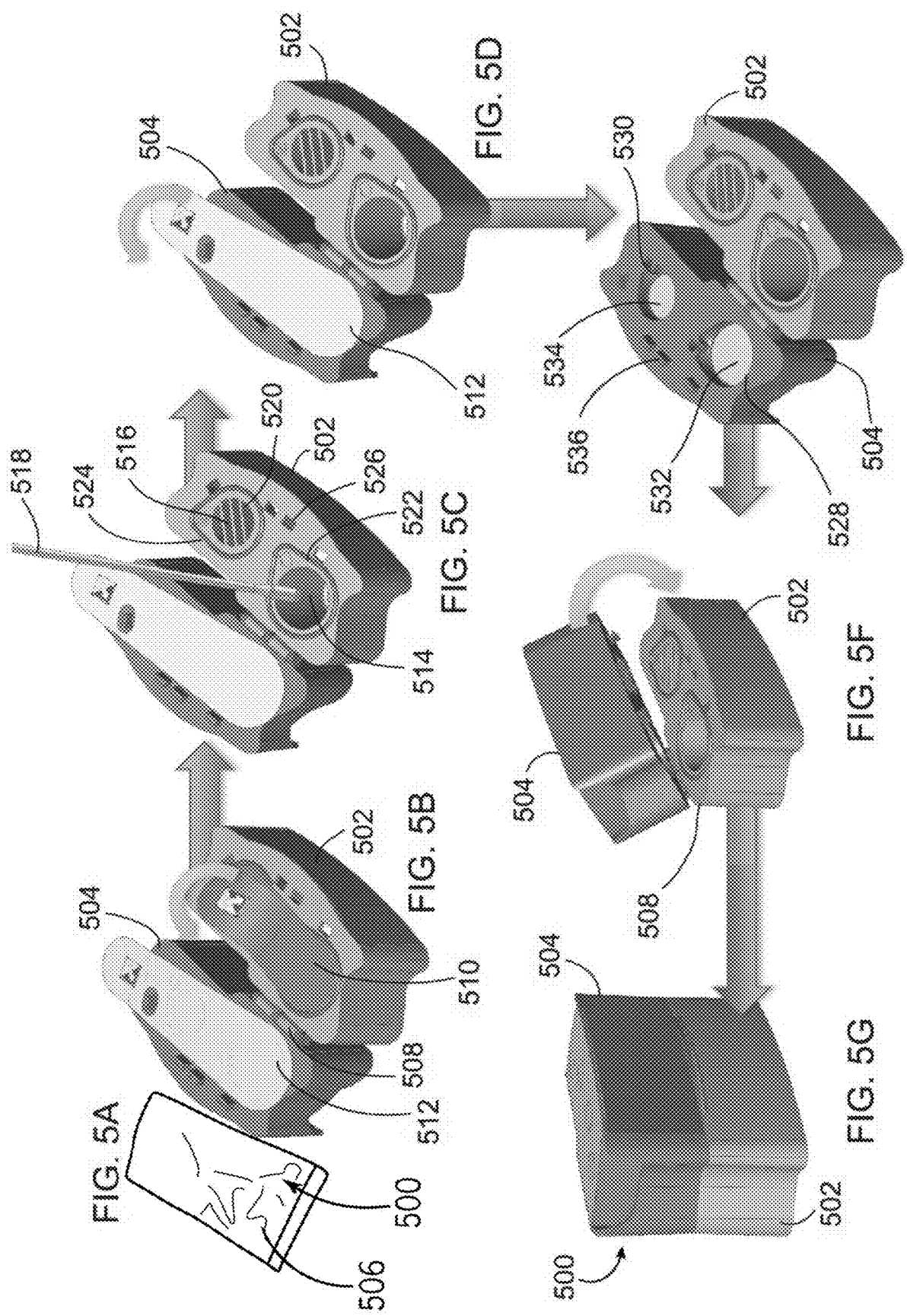

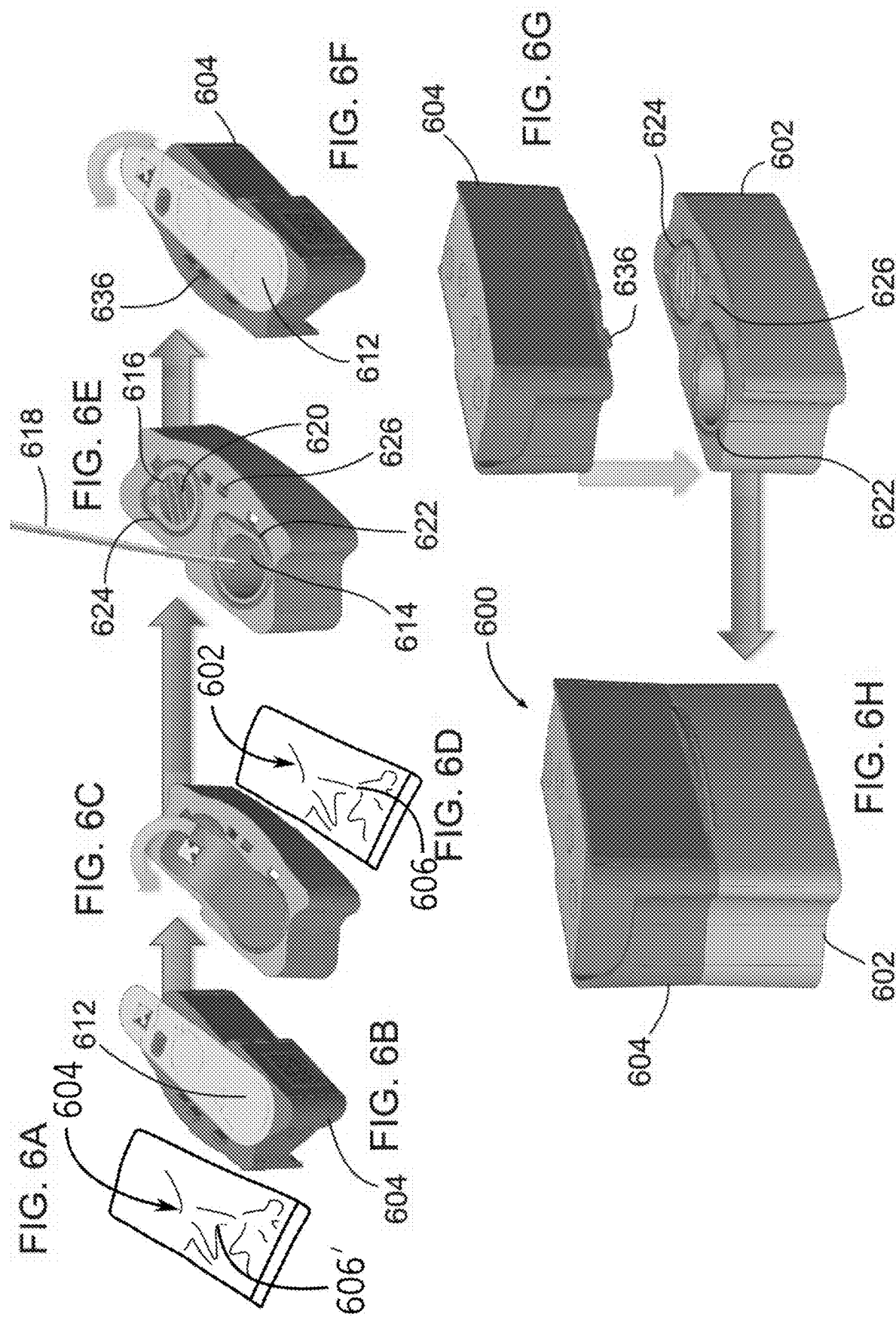

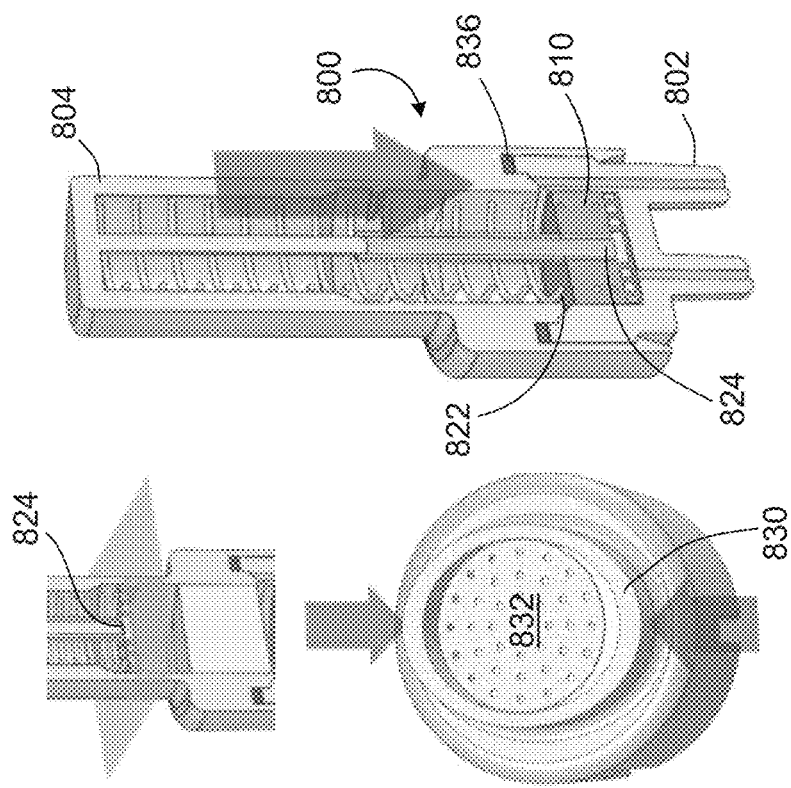
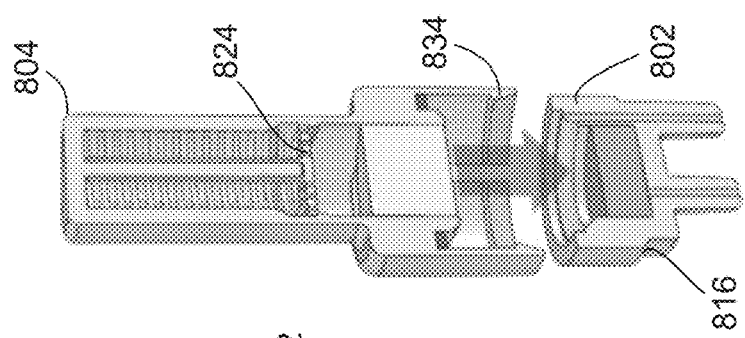
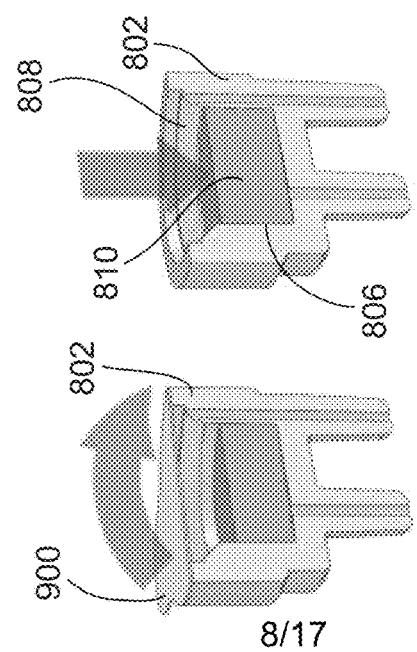
FIG. 9A  FIG. 9B  FIG. 9C  FIG. 9D  FIG. 9E

SEQUENCE LISTING

<160> NUMBER OF SEQ ID NOS: 21

<210> SEQ ID NO 1
<211> LENGTH: 30
<212> TYPE: DNA
<213> ORGANISM: Unknown
<220> FEATURE:
<223> OTHER INFORMATION: Synthetic

<400> SEQUENCE: 1
tgcatgtgtg aggaaggagt tgaaccaaga                                      30

<210> SEQ ID NO 2
<211> LENGTH: 32
<212> TYPE: DNA
<213> ORGANISM: Unknown
<220> FEATURE:
<223> OTHER INFORMATION: Synthetic

<400> SEQUENCE: 2
aaattgcttc tcattgttca ggcacttagg ga                                   32

<210> SEQ ID NO 3
<211> LENGTH: 32
<212> TYPE: DNA

```
<213> ORGANISM: Unknown
<220> FEATURE:
<223> OTHER INFORMATION: Synthetic

<400> SEQUENCE: 3
gaactgagta accttgcaaa rggggaaaag gc                                   32

<210> SEQ ID NO 4
<211> LENGTH: 32
<212> TYPE: DNA
<213> ORGANISM: Unknown
<220> FEATURE:
<223> OTHER INFORMATION: Synthetic

<400> SEQUENCE: 4
gaactgagta accttgcaaa agggggaaaaa gc                                  32

<210> SEQ ID NO 5
<211> LENGTH: 36
<212> TYPE: DNA
<213> ORGANISM: Unknown
<220> FEATURE:
<223> OTHER INFORMATION: Synthetic

<400> SEQUENCE: 5
aytaattgat ggccatccga attcttttgg tcgctg                               36

<210> SEQ ID NO 6
<211> LENGTH: 36
<212> TYPE: DNA
<213> ORGANISM: Unknown
<220> FEATURE:
<223> OTHER INFORMATION: Synthetic

<400> SEQUENCE: 6
aaggattggc tgatgattac ttttggaaaa agaaag                               36

<210> SEQ ID NO 7
<211> LENGTH: 34
<212> TYPE: DNA
<213> ORGANISM: Unknown
<220> FEATURE:
<223> OTHER INFORMATION: Synthetic

<400> SEQUENCE: 7
taattcagcc tgaagttctg tgagtctgct tagc                                 34

<210> SEQ ID NO 8
<211> LENGTH: 34
<212> TYPE: DNA
<213> ORGANISM: Unknown
<220> FEATURE:
<223> OTHER INFORMATION: Synthetic

<400> SEQUENCE: 8
aatcatgaac ctcatggcat cttccctcgc cgcc                                 34

<210> SEQ ID NO 9
<211> LENGTH: 34
<212> TYPE: DNA
<213> ORGANISM: Unknown
<220> FEATURE:
<223> OTHER INFORMATION: Synthetic

<400> SEQUENCE: 9
acaatgcaat catatgcttc tgctatgtta agcg                                 34
```

```
<210> SEQ ID NO 10
<211> LENGTH: 33
<212> TYPE: DNA
<213> ORGANISM: Unknown
<220> FEATURE:
<223> OTHER INFORMATION: Synthetic

<400> SEQUENCE: 10
aacctgggac ctttgatctt gggggggctat atg                                    33

<210> SEQ ID NO 11
<211> LENGTH: 33
<212> TYPE: DNA
<213> ORGANISM: Unknown
<220> FEATURE:
<223> OTHER INFORMATION: Synthetic

<400> SEQUENCE: 11
atgtgttagg aaggagttga accaagaagc att                                     33

<210> SEQ ID NO 12
<211> LENGTH: 48
<212> TYPE: DNA
<213> ORGANISM: Unknown
<220> FEATURE:
<223> OTHER INFORMATION: Synthetic
<220> FEATURE:
<221> NAME/KEY: n
<222> LOCATION: (32)..(32)
<223> OTHER INFORMATION: dT-FAM
<220> FEATURE:
<221> NAME/KEY: misc_feature
<222> LOCATION: (32)..(33)
<223> OTHER INFORMATION: n is a, c, g, t or u
<220> FEATURE:
<221> NAME/KEY: n
<222> LOCATION: (33)..(33)
<223> OTHER INFORMATION: H= THF (abasic site mimic)
<220> FEATURE:
<221> NAME/KEY: n
<222> LOCATION: (35)..(35)
<223> OTHER INFORMATION: dT-BHQ-1
<220> FEATURE:
<221> NAME/KEY: misc_feature
<222> LOCATION: (35)..(35)
<223> OTHER INFORMATION: n is a, c, g, t or u

<400> SEQUENCE: 12
gaaccaagat gcattragca aaacccaggg annantaatc aggcactc                     48

<210> SEQ ID NO 13
<211> LENGTH: 34
<212> TYPE: DNA
<213> ORGANISM: Unknown
<220> FEATURE:
<223> OTHER INFORMATION: Synthetic

<400> SEQUENCE: 13
aatgtgctaa tygggcaagg agacgtggtg ttgg                                    34

<210> SEQ ID NO 14
<211> LENGTH: 32
<212> TYPE: DNA
<213> ORGANISM: Unknown
<220> FEATURE:
<223> OTHER INFORMATION: Synthetic

<400> SEQUENCE: 14
```
ggccatccga attcttttgg tcgctgtctg gc                                     32

<210> SEQ ID NO 15
<211> LENGTH: 50
<212> TYPE: DNA
<213> ORGANISM: Unknown
<220> FEATURE:
<223> OTHER INFORMATION: Synthetic
<220> FEATURE:
<221> NAME/KEY: n
<222> LOCATION: (36)..(36)
<223> OTHER INFORMATION: dT-FAM
<220> FEATURE:
<221> NAME/KEY: misc_feature
<222> LOCATION: (36)..(38)
<223> OTHER INFORMATION: n is a, c, g, t or u
<220> FEATURE:
<221> NAME/KEY: n
<222> LOCATION: (37)..(37)
<223> OTHER INFORMATION: THF (abasic site mimic)
<220> FEATURE:
<221> NAME/KEY: n
<222> LOCATION: (38)..(38)
<223> OTHER INFORMATION: dT-BHQ-1

<400> SEQUENCE: 15
cgaattcttt tggtcgctgt ctggctgtca gtaagnnngc tagagtcccg                  50

<210> SEQ ID NO 16
<211> LENGTH: 33
<212> TYPE: DNA
<213> ORGANISM: Unknown
<220> FEATURE:
<223> OTHER INFORMATION: Synthetic

<400> SEQUENCE: 16
ggaaaaagaa agaaaagctg ggaaatagca tgg                                    33

<210> SEQ ID NO 17
<211> LENGTH: 35
<212> TYPE: DNA
<213> ORGANISM: Unknown
<220> FEATURE:
<223> OTHER INFORMATION: Synthetic

<400> SEQUENCE: 17
gcttagcact ctccctttcc cttcctcatc caatg                                  35

<210> SEQ ID NO 18
<211> LENGTH: 46
<212> TYPE: DNA
<213> ORGANISM: Unknown
<220> FEATURE:
<223> OTHER INFORMATION: Synthetic
<220> FEATURE:
<221> NAME/KEY: n
<222> LOCATION: (29)..(29)
<223> OTHER INFORMATION: dT-FAM
<220> FEATURE:
<221> NAME/KEY: misc_feature
<222> LOCATION: (29)..(29)
<223> OTHER INFORMATION: n is a, c, g, t or u
<220> FEATURE:
<221> NAME/KEY: n
<222> LOCATION: (31)..(31)
<223> OTHER INFORMATION: THF (abasic site mimic)
<220> FEATURE:
<221> NAME/KEY: misc_feature
<222> LOCATION: (31)..(32)
<223> OTHER INFORMATION: n is a, c, g, t or u
<220> FEATURE:
<221> NAME/KEY: n

```
<222> LOCATION: (32)..(32)
<223> OTHER INFORMATION: dT-BHQ-1

<400> SEQUENCE: 18
actgatgata ttcagctaca atcaagacna nncgttaagt aatgaa          46

<210> SEQ ID NO 19
<211> LENGTH: 36
<212> TYPE: DNA
<213> ORGANISM: Unknown
<220> FEATURE:
<223> OTHER INFORMATION: Synthetic

<400> SEQUENCE: 19
ttccagtcag tcctagtcag aaacggtcct tagacg                     36

<210> SEQ ID NO 20
<211> LENGTH: 29
<212> TYPE: DNA
<213> ORGANISM: Unknown
<220> FEATURE:
<223> OTHER INFORMATION: Synthetic

<400> SEQUENCE: 20
gccaggttta tagcacactt gtcacctac                             29

<210> SEQ ID NO 21
<211> LENGTH: 49
<212> TYPE: DNA
<213> ORGANISM: Unknown
<220> FEATURE:
<223> OTHER INFORMATION: Synthetic
<220> FEATURE:
<221> NAME/KEY: n
<222> LOCATION: (31)..(31)
<223> OTHER INFORMATION: dT-FAM
<220> FEATURE:
<221> NAME/KEY: misc_feature
<222> LOCATION: (31)..(31)
<223> OTHER INFORMATION: n is a, c, g, t or u
<220> FEATURE:
<221> NAME/KEY: n
<222> LOCATION: (33)..(33)
<223> OTHER INFORMATION: THF (abasic site mimic)
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: n
<222> LOCATION: (35)..(35)
<223> OTHER INFORMATION: dT-BHQ-1
<220> FEATURE:
<221> NAME/KEY: misc_feature
<222> LOCATION: (35)..(35)
<223> OTHER INFORMATION: n is a, c, g, t or u

<400> SEQUENCE: 21
gccaggttta tagcacactt gtcacctaca ntncngattg gtggactct       49
```

AUTOMATED NESTED RECOMBINASE POLYMERASE AMPLIFICATION

CROSS-REFERENCE TO RELATED APPLICATION

This application is a 371 U.S. National Phase Entry of pending International Application No. PCT/US2017/020782, filed Mar. 3, 2017, which claims the benefit of U.S. Patent Application Ser. No. 62/303,934 entitled "AUTOMATED NESTED RECOMBINASE POLYMERASE AMPLIFICATION" filed Mar. 4, 2016, each of which is hereby incorporated by reference in its entirety.

STATEMENT OF GOVERNMENT INTEREST

This invention was made with government support under HHSO100201400011C awarded by the U.S. Department of Health and Human Services. The government has certain rights in the invention.

TECHNICAL FIELD

This invention relates to a flu assay system, and more particularly to a system including a sample module, a microfluidic nucleic acid amplification device, and an analyzer to facilitate fully automated nested recombinase polymerase amplification (RPA) on a sample delivered to the nucleic acid amplification device via the sample module.

BACKGROUND

Detection of trace levels of polynucleotide sequences can play a significant role in the detection of pathogens and genetic disease and with helping to tailor treatment regimens to particular infections or genotypes. Certain isothermal nucleic acid amplification methods are able to amplify target polynucleotide sequences from trace levels to very high and detectable levels within a matter of minutes. Such isothermal methods, e.g., Recombinase Polymerase Amplification (RPA) or Nicking and Extension Amplification Reaction (NEAR), can allow users to detect a particular sequence in trace amounts, facilitating point-of-care testing and increasing the accessibility and speed of diagnostics.

SUMMARY

Nucleic acid amplification devices disclosed herein are constructed to include an array of microfluidic channels that interconnect primary and secondary reaction chambers to detection chambers. Integrated pump modules are also provided to permit selective movement of liquid through the device at appropriate times. A primary reaction chamber is provided, in which a first round of RPA occurs, which results in amplification of a target polynucleotide sequence of interest. Following the first round of RPA, sample liquid is combined with specific RPA primers and moved to a secondary reaction chamber. During secondary amplification, a sequence completely contained within the primary reaction product is amplified to form secondary reaction products; following which detection of the secondary reaction products is performed. Detection may be achieved using optical or electrochemical means.

A product mixture from a first round of RPA may be separated into a plurality of streams and passed through reagent reservoirs, in which the product mixture is combined with the same or different RPA primers, before entering a plurality of secondary reaction chambers. In this manner, a nucleic acid amplification device may be used to detect more than one target of interest (e.g., influenza A virus and influenza B virus). In some cases, one of the secondary reaction chambers may be used as a control.

A first general aspect includes providing a sample to a microfluidic device, and amplifying a target polynucleotide sequence in the sample. Amplifying the target polynucleotide sequence includes performing a first round of amplification on the sample to yield a first amplification product, and performing a second round of amplification on the first amplification product to yield a second amplification product. The second amplification product includes a smaller sequence completely contained within the first amplification product produced during the first round of amplification.

Implementations of the first general aspect may include one or more of the following features.

Some implementations include detecting the second amplification product.

In some embodiments, detecting the second amplification product may include labeling the second amplification product with a first oligonucleotide linked to a fluorophore and a quencher to yield a labeled second product, cleaving the quencher from the labeled second amplification product, and optically detecting a signal from the fluorophore, wherein a detectable signal is indicative of the presence of the second amplification product. Cleaving the quencher may be performed using a nuclease. The nuclease may target double-stranded DNA. In some cases, the nuclease is formamidopyrimine-DNA glycosylase.

In some embodiments, detecting the second amplification product includes labeling the second amplification product with a first oligonucleotide linked to a redox moiety to yield a labeled second amplification product, cleaving the redox moiety from the labeled second amplification product, and electrochemically detecting a signal from the cleaved redox moiety, wherein a detectable signal is indicative of the presence of the second amplification product. The redox moiety is typically selected from the group consisting of phenothiazine, a phenoxazine, a ferrocene, ferricyanide, ruthenium (III), osmium (II), an anthraquinone, a phenazine, and derivatives thereof. Cleaving the redox moiety may be performed using a nuclease. The nuclease may target double-stranded DNA. In some cases, the nuclease is formamidopyrimine-DNA glycosylase.

Some implementations include performing a third round of amplification on the second amplification product to yield a third amplification product, and detecting the third amplification product, wherein the third amplification product includes a smaller sequence completely contained within the second amplification product produced during the second round of amplification.

The sample may be obtained from an animal. For instance, the sample may be obtained from the blood, sputum, mucus, saliva, tears, or urine of the animal. In some cases, the sample is obtained from a human.

A target nucleic acid may include the target polynucleotide sequence. In some embodiments, the target nucleic acid is obtained from an animal pathogen. The animal pathogen may be a single-stranded DNA virus, double-stranded DNA virus, or single-stranded RNA virus. The animal pathogen may be a bacterium. The target nucleic acid may be double-stranded DNA, single-stranded DNA, or RNA. In some cases, the target nucleic acid is selected from the group consisting of genomic DNA, plasmid DNA, viral DNA, mitochondrial DNA, cDNA, synthetic double-stranded DNA and synthetic single-stranded DNA. The target nucleic acid may be viral DNA or viral RNA. In certain cases, the animal pathogen is an influenza A virus or an influenza B virus.

In some implementations, two or more target polynucleotide sequences in the sample are amplified. In one example, a target polynucleotide sequence including an influenza A gene sequence and a target polynucleotide sequence including an influenza B gene sequence are amplified.

In some implementations, two or more second amplification products are detected. In certain implementations, a second amplification product including an influenza A gene sequence and a second amplification product including an influenza B gene sequence are detected.

In a second general aspect, a diagnostic card includes a card body. The card body includes a primary reaction chamber, one or more secondary reaction chambers, a passage for supplying the sample fluid to the primary reaction chamber, one or more detection chambers in fluidic connection with the one or more secondary reaction chambers, and a detection module associated with each detection chamber. The primary reaction chamber is configured to carry out a first nucleic acid amplification on a sample fluid in the reaction chamber to form a first amplification product. Each secondary reaction chamber is configured to carry out a second nucleic amplification on the first amplification product to form second amplification products Implementations of the second general aspect may include one or more of the following features.

In some embodiments, the detection module is an optical module, such as a fluorescence detector. The fluorescence detector may include a single light pipe to direct illumination light to the one or more detection chambers, and discrete light pipes to receive reflected light from each detection chamber.

In some embodiments, the detection module is an electrode module. The detection module may include a series of conductive tracks terminating in electrodes for each detection chamber. The device may include additional conductive tracks and electrodes to detect position of liquid throughout the microfluidic card.

In some implementations, the amplification includes a recombinase polymerase amplification (RPA) reaction.

In some implementations, the diagnostic card includes mixing means, pumps, and connection ports for connecting to a sample module. The primary reaction chamber may be coupled to a heater. The primary reaction chamber may include a mixing means or be coupled to a mixing means. In some cases, the primary reaction chamber includes a reagent. The reagent may include a RPA reagent. The RPA reagent may be freeze dried.

In some implementations, each secondary reaction chamber includes a reagent. The reagent may include a RPA reagent. The RPA regent may be freeze dried.

In some implementations, the sample fluid is a sample obtained from an animal. The sample may be obtained from the blood, sputum, mucus, saliva, tears, or urine of the animal. In some cases, the sample fluid is a sample obtained from a human. The sample fluid may include a target nucleic acid. The target nucleic acid may be obtained from an animal pathogen. The animal pathogen may be a single-stranded DNA virus, double-stranded DNA virus, or single-stranded RNA virus. In some cases, the animal pathogen is a bacterium. The target nucleic acid may be double-stranded DNA, single-stranded DNA, or RNA. In certain cases, the target nucleic acid is selected from the group consisting of genomic DNA, plasmid DNA, viral DNA, mitochondrial DNA, cDNA, synthetic double-stranded DNA and synthetic single-stranded DNA. The target nucleic acid may be viral DNA or viral RNA. The animal pathogen may be influenza A virus or influenza B virus.

In some implementations, the second amplification products are produced 30 minutes or less, 15 minutes or less, 10 minutes or less, or 5 minutes or less after delivery of the sample fluid to the diagnostic card. The diagnostic card is typically disposable.

In some implementations, the diagnostic card includes additional reaction chambers, each configured to carry out an additional round of nucleic acid amplification reactions to form additional amplified products, such that the amplification product from each successive n+1 round of amplification is a smaller sequence completely contained within the amplification product of the prior nth round.

A third general aspect includes a reader configured to receive the diagnostic card of the second general aspect. The reader includes a detector configured to detect the presence of the second amplified products in the secondary reaction chambers.

A fourth general aspect includes a nucleic acid amplification device. The nucleic acid amplification device includes a first reaction chamber fluidically coupled to a first inlet port and a first outlet port, second reaction chambers fluidically coupled to a second inlet port and a second outlet port, detection chambers, a first pump, a second pump, and a third pump. The first inlet port is fluidically coupled to the first reaction chamber via a first pump, and the first outlet port is fluidically coupled to the first reaction chamber. The first reaction chamber is fluidically coupled to the second reaction chambers via the second pump, and the second outlet port is fluidically coupled to the second reaction chambers. The second inlet port is fluidically coupled to the second reaction chambers via the third pump.

Implementations of the fourth general aspect may include one or more of the following features.

In some implementations, the nucleic acid amplification device is a microfluidic device. The first reaction chamber typically includes a reagent. In some cases, the first reaction chamber includes a catalyst. The catalyst may include magnesium.

In some implementations, the nucleic acid amplification device includes reagent reservoirs, and the second pump and the third pump are fluidically coupled to each second reaction chamber via a first reagent reservoir. The second pump and the third pump may be fluidically coupled to each second reaction chamber via a first reagent reservoir and a second reagent reservoir. In some cases, the first reagent reservoir and the second reagent reservoir are in series. The first reagent reservoir may include oligomers. The second reagent reservoir may include magnesium.

In some implementations, each second reaction chamber is a detection chamber. A portion of each detection chamber may be optically transparent. In some cases, electrodes are coupled to each detection chamber. In one example, three electrodes are coupled to each detection chamber.

In some implementations, the nucleic acid amplification device includes fluid detection regions. The first pump and the first reaction chamber may be coupled via a first detection region. The second pump and the second reaction chambers may be coupled via a second detection region. The third pump and the second reaction chambers may be coupled via a third detection region. The third pump and the first reaction chamber may be coupled via a fourth detection region. In some cases, a portion of each detection region is optically transparent. A flow detection chamber may be coupled to each detection region.

In some implementations, the nucleic acid amplification device includes a heater coupled to the first reaction chamber. The first reaction chamber may include a stirrer. In certain implementations, the first pump is configured to provide a sample delivered to the nucleic acid amplification device via the first inlet port to the first reaction chamber. The second and third pumps may be configured to combine a reagent delivered to the nucleic acid amplification device body via the second inlet port with a product from the first reaction chamber to yield a reactant mixture. The second and third pumps may be configured to provide a portion of the reactant mixture to each of the second reaction chambers.

Other features and advantages of the invention will be apparent from the following detailed description and figures, and from the claims.

DESCRIPTION OF DRAWINGS

FIGS. 1A-1D depict components of a system for conducting fully automated nested RPA on a sample delivered to a nucleic acid amplification device via a sample module.

FIGS. 2A-2E depicts an alternative workflow for the system depicted in FIG. 1.

FIGS. 3A and 3B depict perspective views of a receiver module portion of a sample module.

FIGS. 4A and 4B depict perspective views of a transfer module portion of a sample module.

FIGS. 5A-5G depict a workflow for providing a sample to a sample module having a coupled receiver module and transfer module.

FIGS. 6A-6H depict a workflow for providing a sample to a sample module having a separate receiver module and transfer module.

FIGS. 9A-9E depict a workflow for providing a sample to the sample module depicted in FIGS. 8A and 8B.

DETAILED DESCRIPTION

Figure 7:
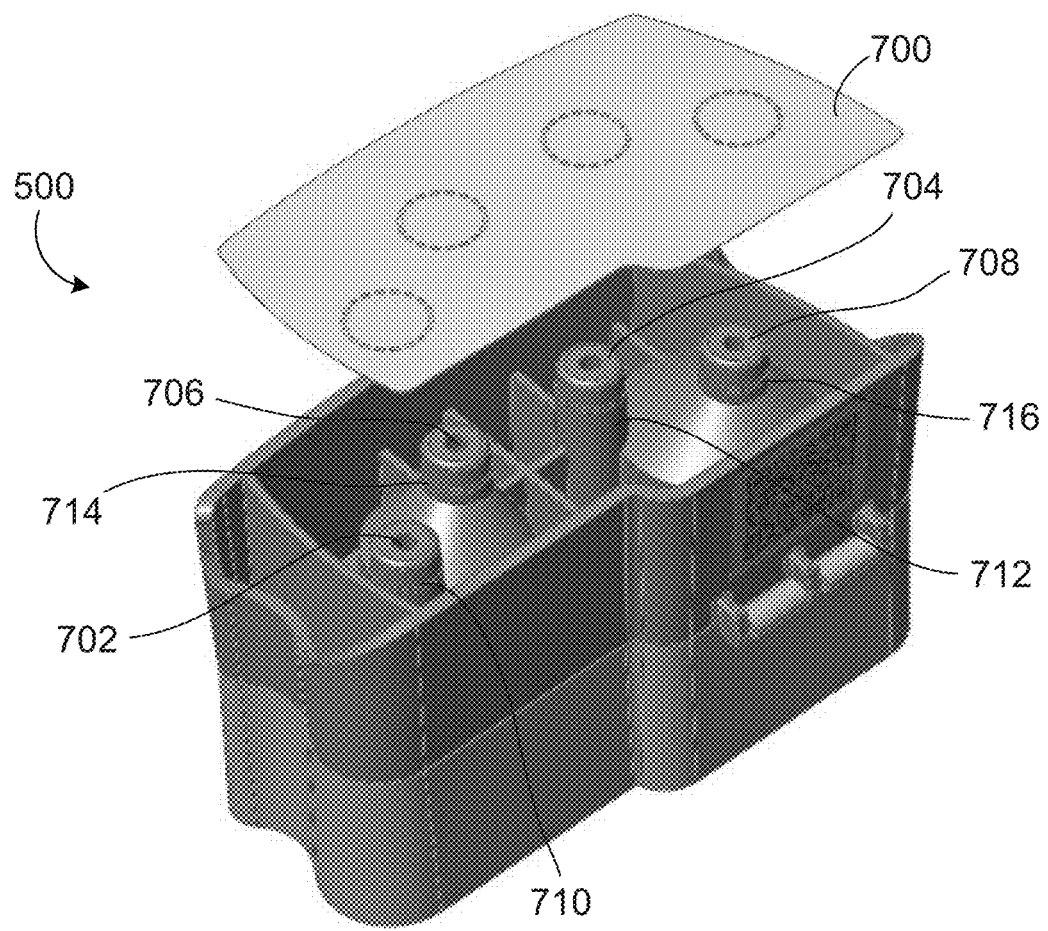
FIG. 7 depicts a perspective view of a hinged sample module.

FIGS. 1A-1D depict components of system 100 for conducting fully automated nested RPA on a sample provided to a microfluidic nucleic acid amplification device. FIG. 1A depicts sample module 102, which includes receiver module 104 and transfer module 106. FIG. 1B depicts microfluidic nucleic acid amplification device 110. As depicted in FIG. 1C, sample module 102 and nucleic acid amplification device 108 are coupled to form nucleic acid amplification assembly 110. FIG. 1D depicts system 100, including nucleic acid amplification assembly 110 inserted in analyzer 112 for assessment of the presence of a target nucleic acid in a sample provided to nucleic acid amplification device 108 from sample module 102.

System 100 is used to assess the presence of a target nucleic acid in a sample provided to receiver module 104 of sample module 102. Receiver module 104 and transfer module 106 of sample module 102, as well as nucleic acid amplification device 108, contain reagents required to perform a first round of RPA, followed by subsequent second rounds of RPA to amplify the target nucleic acid, if present in the sample. Coupling sample module 102 and nucleic acid amplification device 108 creates fluidic pathways between the sample module and the nucleic acid amplification device, allowing delivery of a RPA reaction mixture to the nucleic acid amplification device. In some cases, system 100 is used to assess the presence of two or more target nucleic acids in a sample. In one example, system 100 is used to assess the presence of influenza A virus and influenza B virus in a sample. In certain cases, sample module 102 and nucleic acid amplification device 108 are configured to perform three or more rounds of nested RPA.

FIGS. 2A-2E depict an alternative workflow for system 100. As depicted in FIG. 2A, which nucleic acid amplification device 108 is inserted into analyzer 112. In FIG. 2B, sample module 102 is advanced toward nucleic acid amplification device 108 in analyzer. Registration features on analyzer 112 interface constrain sample module 102 in two dimensions prior to coupling, allowing the sample module and nucleic acid amplification device 108 to be mated to form passageways that allow fluid to pass from the sample module to the nucleic acid amplification device and vice versa. FIG. 2C depicts nucleic acid amplification assembly 110 in analyzer 112. Coupling of sample module 102 to nucleic acid amplification device 108 may initiate the flow of reactants from the sample module to the nucleic acid amplification device, thereby initiating assessment of the presence of the target nucleic acid in the sample. Once the assessment is complete, as depicted in FIG. 2D, registration features in analyzer 112 may be engaged to release nucleic acid amplification assembly 110. FIG. 2E depicts nucleic acid amplification assembly 110 after release from analyzer 112. Nucleic acid amplification assembly 110 may be disposed of after release from analyzer 112.

FIGS. 3A and 3B depict perspective views of an embodiment of receiver module 104 of sample module 102. FIG. 3A depicts a perspective view of receiver module 104 with chambers 300 for receiving a sample, containing a reagent, or both. Receiver module 104 also includes registration features 302 for aligning the receiver module with a transfer module. FIG. 3B depicts a perspective view opposite that of FIG. 3A, which depicts an exterior view of the bottoms 304 of chambers 300.

FIGS. 4A and 4B depict perspective views of an embodiment of a transfer module 106 configured to mate with a receiver module. FIG. 4A depicts a perspective view of transfer module 106 with chambers 400, each chamber having an inlet port 402 and an outlet port 404. Transfer module 106 also includes registration features 406 for aligning the transfer module with the receiver module. FIG.

4B depicts a perspective view opposite that of FIG. 4A, which depicts an exterior view of the bottoms 408, as well as inlet ports 402 and outlet ports 404 of chambers 400.

FIGS. 5A-5G depicts a workflow for providing a sample to sample module 500 having a coupled receiver module 502 and transfer module 504. As depicted in FIG. 5A, sample module 500 may be provided in sealed pouch 506. Sealed pouch 506 may be a foil pouch. FIG. 5B depicts sample module 500 after removal from pouch 506, with hinge 508 opened to expose hermetic seals 510 and 512 on receiver module 502 and transfer module 504, respectively.

As depicted in FIG. 5C, a seal may be removed from receiver module 502 to expose sample chamber 514 and blank chamber 516. Sample chamber 514 and blank chamber 516 typically include a liquid medium, such as a buffer solution. A sample (e.g., a body fluid) may be delivered to sample chamber 514 via device 518 (e.g., a swab), thereby introducing the sample to the liquid medium in sample chamber 514. Blank chamber 516 may be covered with occluding element 520 to prevent insertion of a sample in the blank chamber. Gaskets 522 and 524 may be positioned about an exterior of sample chamber 514 and blank chamber 516, respectively, to promote seal formation between receiver module 502 and the transfer module after a sample has been deposited in sample chamber 514. Registration features 526 on receiver module 502 are configured to mate with corresponding registration features on the transfer module.

As depicted in FIGS. 5D and 5E, seal 512 may be removed from transfer module 504 to expose sample chamber 528 and blank chamber 530. Retaining elements 532 and 534 may be positioned in sample chamber 528 and blank chamber 530, respectively, to retain a solid reagent in the sample chamber, the blank chamber, or both. In one example, retaining element 532 retains a reagent pellet in sample chamber 528. The reagent pellet may include oligomers for a RPA reaction. In some cases, the pellet is a freeze dried pellet. Blank chamber 530 may be free of a solid reagent. Retaining elements 532 and 534 typically define openings, such as pores. In some cases, retaining elements 532 and 534 are frits. Frits may be selected to facilitate transfer of the fluid from receiver module 502 to transfer module 504. In one example, retaining elements 532 and 534 are hydrophilic frits. Transfer module 504 includes registration features configured to mate with registration features of receiver module 502.

After seal 512 is removed from transfer module 504, as depicted in FIG. 5F, the transfer module may be rotated about hinge 508 and secured to receiver module 502, with retaining elements retaining reagents present in the sample chamber and the blank chamber. When receiver module 502 and transfer module 504 are pressed together, as depicted in FIG. 5G, registration features 526 and 536 lockingly engage, gasket 522 seals the sample chambers together, and gasket 524 seals the blank chambers together. When sample module 502 is oriented as depicted with transfer module 504 above receiver module 502, before inversion has occurred, the liquid medium in sample chamber 514 and blank chamber 516 remains in the receiver module and does not flow toward the sample chamber and the blank chamber, respectively, in transfer module 504. Registration features 526 and 536 may be configured to irreversibly seal receiver module 502 and transfer module 504 such that sample module 500 cannot be opened unintentionally.

Prior to coupling sample module 500 to a nucleic acid amplification device, the sample module is inverted to cause movement of the liquid medium in receiver module 502 toward transfer module 504, thereby hydrating solid reagents in the transfer module to form hydrated reaction mixtures. In one example, freeze dried RPA reagents in the transfer module are hydrated to form a hydrated reaction mixture.

FIGS. 6A-6H depict an alternative workflow for providing a sample to sample module 600 having a separate receiver module 602 and transfer module 604. As depicted in FIG. 6A, receiver module 602 and transfer module 604 may each be provided in a separate sealed pouch 606, 606'. Sealed pouch 606 may be a foil pouch.

FIG. 6B depicts transfer module 604 after removal from sealed pouch 606'. Transfer module 604 is sealed with seal 612. FIG. 6C depicts receiver module 602 removed from pouch 606. Receiver module 602 is sealed with a seal. After removal of the seal from receiver module 602, as depicted in FIG. 6D, sample chamber 614 and blank chamber 616 are exposed. Sample chamber 614 and blank chamber 616 typically include a liquid medium, such as a buffer solution. A sample (e.g., a body fluid) may be delivered to sample chamber 614 via device 618 (e.g., a swab), thereby introducing the sample to the liquid medium in the sample chamber. Blank chamber 616 may be covered with occluding element 620 to prevent insertion of a sample in the blank chamber. Gaskets 622 and 624 may be positioned about an exterior of sample chamber 614 and blank chamber 616, respectively, to promote seal formation between receiver module 602 and transfer module 604. Registration features 626 on receiver module 602 are configured to mate with corresponding registration features on transfer module 604.

As depicted in FIG. 6E, seal 612 may be removed from transfer module 604. Removing seal 612 from transfer module 604 exposes a sample chamber and a blank chamber (not shown). Retaining elements (not shown) may be positioned in the sample chamber and blank chamber, respectively, to retain a solid reagent in the sample chamber, the blank chamber, or both. In one example, the solid reagent includes oligomers for a RPA reaction. In some cases, the solid reagent is a freeze dried pellet. The blank chamber may be free of a solid reagent. The retaining elements typically define openings, such as pores. In some cases, the retaining elements are frits. Frits may be selected to facilitate transfer of the fluid from receiver module 602 to transfer module 604. In one example, the retaining elements are hydrophilic frits. Transfer module 602 includes registration features 636 configured to mate with registration features 626 of receiver module 602.

After seal 612 is removed from transfer module 604, as depicted in FIG. 6F, the transfer module may be inverted to align registration features 626 and 636. During this inversion, retaining elements in transfer module 604 retain reagents present in the sample chamber and blank chamber of the transfer module. When receiver module 602 and transfer module 604 are pressed together, as depicted in FIG. 6G, registration features 626 and 636 lockingly engage, gasket 622 seals the sample chambers of the receiver and transfer modules together, and gasket 624 seals the blank chambers of the receiver and transfer modules together. With transfer module 604 above receiver module 602 as depicted in FIG. 6G, the liquid medium in sample chamber 614 and blank chamber 616 remains in the receiver module and does not flow toward the sample chamber and the blank chamber in the transfer module, respectively. Registration features 626 and 636 may be configured to irreversibly seal receiver module 602 and transfer module 604, as depicted in FIG. 6H, such that sample module 600 cannot be opened unintentionally.

Prior to coupling sample module 600 to a nucleic acid amplification device, the sample module may be inverted to cause movement of the liquid medium in receiver module 602 toward transfer module 604, thereby hydrating solid reagents in the transfer module to form hydrated reaction mixtures. In one example, freeze dried RPA reagents in the transfer module are hydrated to form a hydrated reaction mixture.

FIG. 7 is a perspective view of sample module 500. Transfer module 500 may be packaged with seal 700 covering the portion of the transfer module configured to couple to the nucleic acid amplification device. Seal 700 may be a foil seal that provides an opaque surface to cover openings of inlet ports 702 and 704 and outlet ports 706 and 708. Seal 700 may retain the hydrated reaction mixture in sample module 500 upon inversion. In some cases, seal 700 is removed from sample module 500, nucleic acid amplification device is coupled to the sample device, and the sample module 500 is first inverted after it is sealed to the nucleic acid amplification device. Inlet ports 702 and 704 and outlet ports 706 and 708 may have tapered ends (e.g., low profile luer connectors) configured to be inserted into a nucleic acid amplification device. In some cases, gaskets 710, 712, 714, and 716 may be positioned on inlet ports 702, 704, 706, and 708, respectively, to form an air-tight seal with a nucleic acid amplification device.

Figures 8A, 8B:
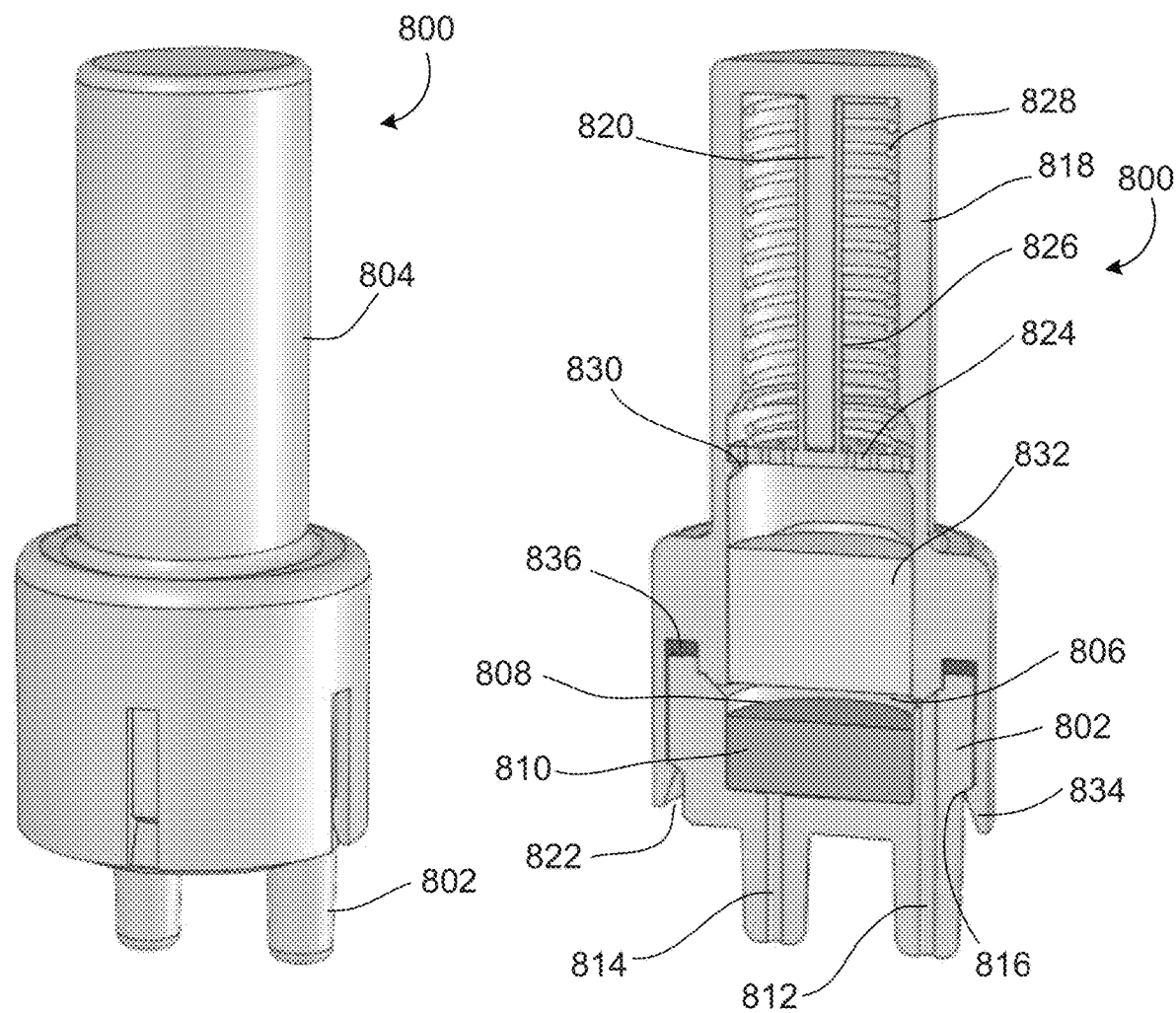
FIGS. 8A and 8B depict views of an alternative sample module.

FIGS. 8A and 8B depict an alternative embodiment of a sample module. FIG. 8A is a perspective view of sample module 800 including receiver module 802 and transfer module 804. FIG. 8B is a perspective cross-sectional view of sample module 800. As depicted in FIG. 8B, receiver module 802 defines sample chamber 806 having opening 808. Sample chamber 806 holds liquid medium 810. Liquid medium 810 may be a buffer solution. Receiver module 802 includes inlet port 812 and outlet port 814. Receiver module 802 also includes registration feature 816 configured to engage a registration feature of transfer module 804.

Transfer module 804 includes housing 818 having extension 820 and defining opening 822 configured to accept sample chamber 806 of receiver module 802. Ram 824 is positioned in housing, with extension 820 positioned in arm 826 of ram. Arm 826 is positioned within spring 828, and the spring is held in a loaded position with release catch 830. Porous element 832 is positioned between ram 824 and opening 822. Porous element 832 contains a solid reagent (e.g., a freeze dried RPA reagent). Registration feature 834 is configured to engage with registration feature 816 of receiver module 802, and gasket 836 forms a seal between the receiver module and transfer module 804. As depicted, receiver module 802 is seated in opening 822 of transfer module 804. Registration features 816 and 834 lockingly engage to seal receiver module 802 and transfer module 804 via gasket 836. Registration features 816 and 834 may be configured to irreversibly seal receiver module 802 and transfer module 804 such that sample module 800 cannot be opened unintentionally.

FIGS. 9A-9E depict a workflow for providing a sample to sample module 800. In FIG. 9A, seal 900 is removed from receiver module 802. In FIG. 9B, a sample is provided to liquid medium 810 in sample chamber 806 of receiver module 802 via opening 808. In FIG. 9C, transfer module 804 is advanced toward receiver module 802 to lockingly engage registration features 816 and 834. After receiver module 802 is sealed to transfer module 804 via gasket 836, force may be applied to release catch 830 to release spring-loaded ram 824, as depicted in FIG. 9D. Releasing spring-loaded ram 824 advances porous element 832 through opening 822, such that the solid reagent in the porous element is hydrated in liquid medium 810 of receiver module 802. FIG. 9E depicts sealed sample module 800 with ram 824 resting in receiver module 802, having forced the solid reagent porous element 832 into liquid medium 810. Sealed sample module 800 may be coupled to a nucleic acid amplification device to assess the presence of a target nucleic acid in the sample provided to the receiver module 802.

Figure 10:
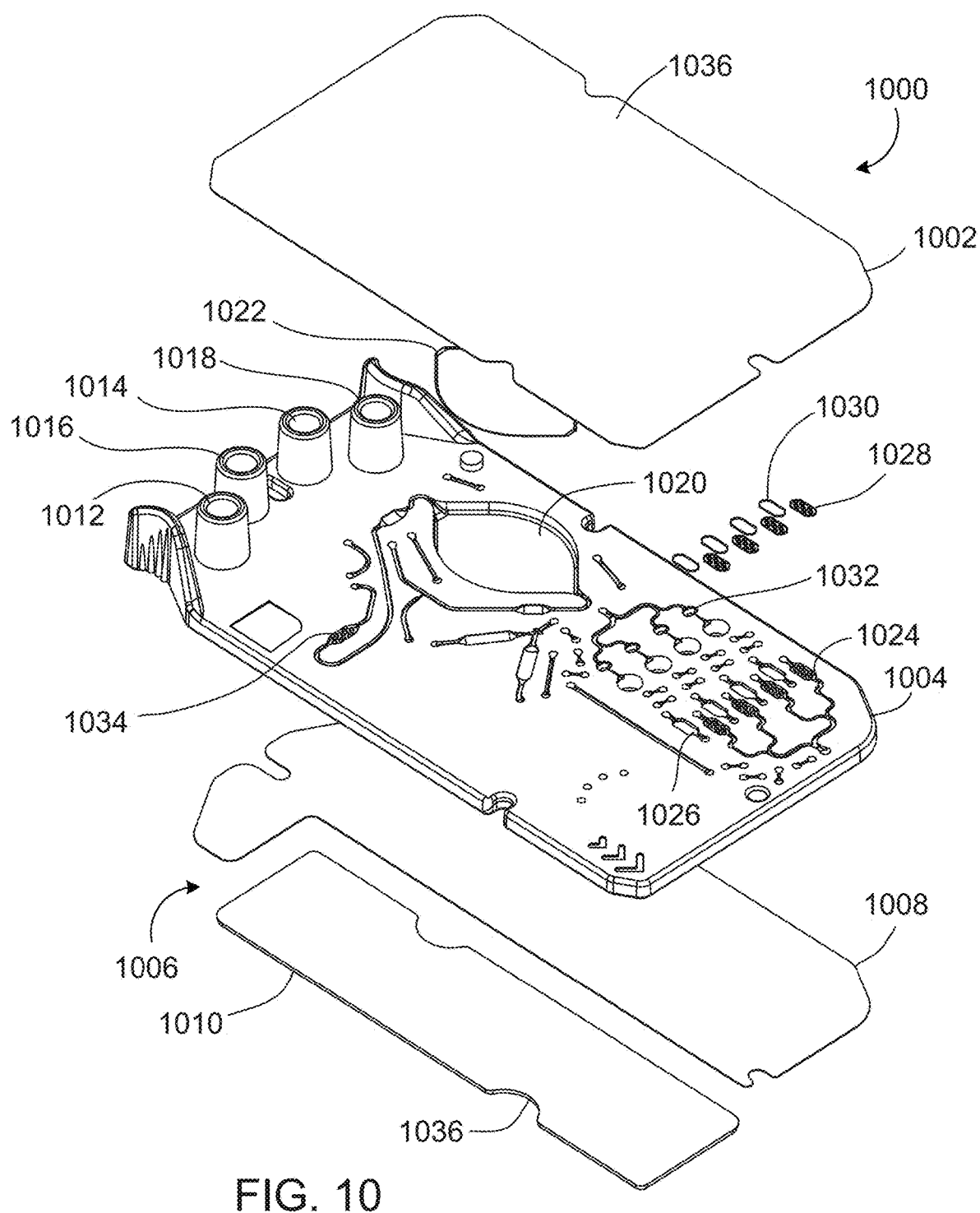
FIG. 10 depicts an exploded view of a microfluidic nucleic acid amplification device for detection of optical probes.

FIG. 10 depicts an exploded view of nucleic acid amplification device 1000 for optical detection. Nucleic acid amplification device 1000 is a laminated microfluidic device including top layer 1002, intermediate layer 1004, and base layer 1006. Base layer 1006 may include more than one component. As depicted, base layer 1006 include two components 1008 and 1010.

Intermediate layer 1004 includes inlet ports 1012 and 1014 and outlet ports 1016 and 1018, which couple to outlet ports and inlet ports, respectively, of a sample module. Intermediate layer 1004 typically includes reagents, such as RPA reagents. As depicted in FIG. 10, primary reaction chamber 1020 includes a solid reagent 1022 (e.g., $Mg^{2+}$ in the form of magnesium acetate). Intermediate layer 1004 includes reagent reservoirs 1024 and 1026, which contain solid reagents 1028 and 1030. In one example, solid reagent 1028 includes dried (e.g., freeze dried) oligomers and solid reagent 1030 includes $Mg^{2+}$ (e.g., in the form of magnesium acetate). Secondary reaction chambers 1032 may also function as detection chambers, in which target nucleic acids are detected via optical signals by an analyzer. Secondary reaction chambers 1032 have an optically transparent covering, such that fluorescent signals generated when the fluorophore and quencher are separated via an exonuclease can be detected by optical sensors in the analyzer in which the nucleic acid amplification device is configured to be inserted. Registration features 1036 allow alignment of nucleic acid amplification device 1000 in an analyzer.

Intermediate layer 1004 may also include flow detection chambers 1034, each having a transparent covering through which the presence of fluid is monitored optically by an analyzer to detect a flow of liquid. An analyzer configured to accept nucleic acid amplification device 1000 includes a light source directed toward each flow detection chamber configured. The analyzer is configured to detect (e.g., via light scattering) the presence of liquid in each flow detection chamber. Detection of liquid in a flow detection chamber may trigger various operations (e.g., initiation or cessation of pumping), and a controller in the analyzer may be configured to implement various parameters (e.g., pumping time, reaction time, mixing time, flow time) based on detection of a liquid in a flow detection chamber, such that reagents are provided in pre-determined volumes and allowed to react for pre-determined times.

Nucleic acid amplification device 1000 may include additional features not depicted in FIG. 10, such as pumps and microfluidic pathways. One or more of the pumps may be a peristaltic pump or a syringe pump. The pumps may selectively drive reagents from the sample module and the primary reaction chamber 1020 toward secondary reaction chambers 1032 based on elapsed time or flow of fluid through flow detection chambers detected by optical sensors in an optical analyzer, metering aliquots as needed.

Figure 11:
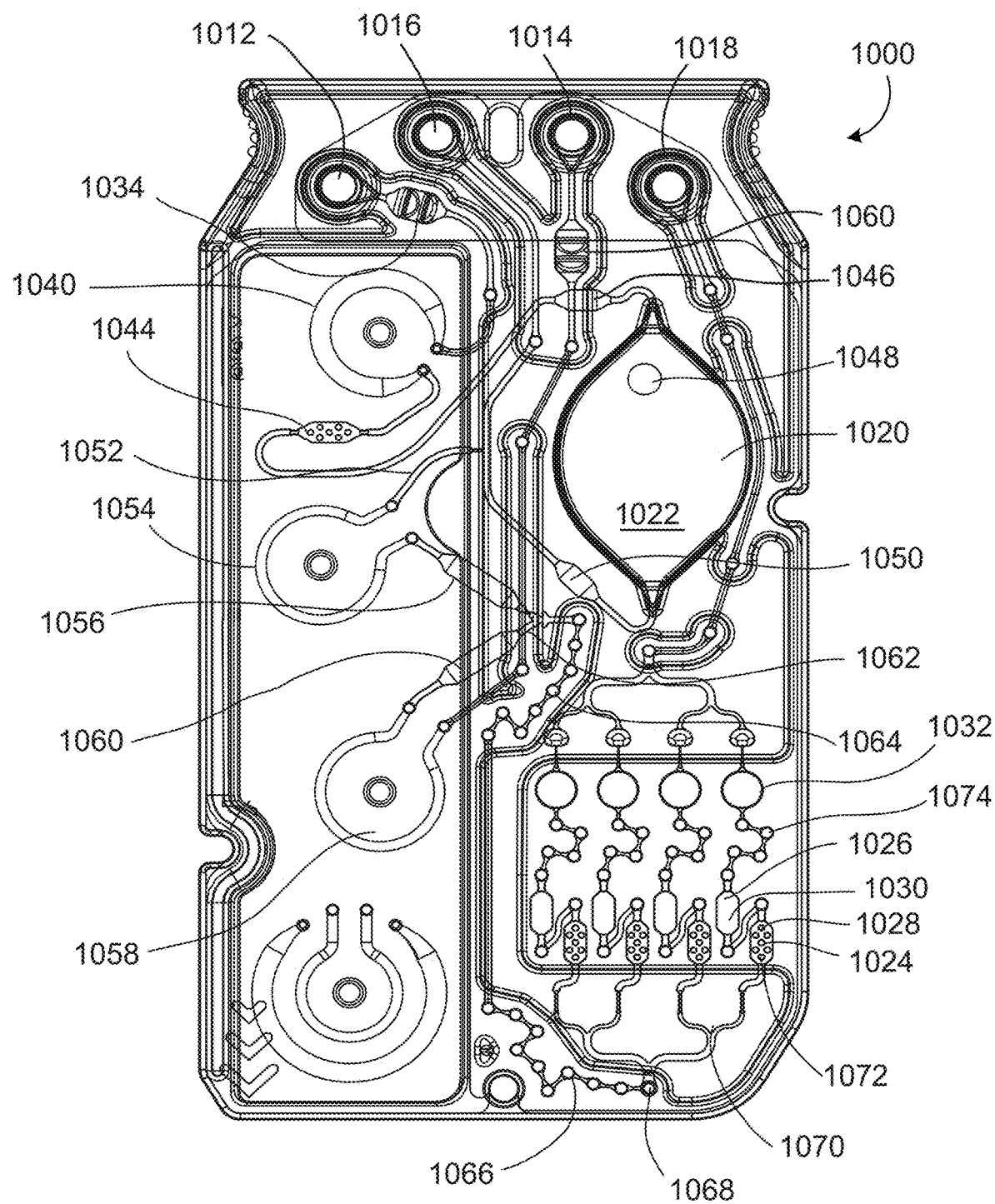
FIG. 11 depicts the working components of the microfluidic nucleic acid amplification device depicted in FIG. 10.

Operation of nucleic acid amplification device 1000 with a sample module is described with respect to FIG. 11. When a sample module is coupled to nucleic acid amplification device 1000, outlet ports of the sample module are coupled to inlet ports 1012 and 1014 of the nucleic acid amplification device, and inlet ports of the sample module are coupled to outlet ports 1016 and 1018 of the nucleic acid amplification device. Reagents in the sample module flow into inlet ports 1012 and 1014 of nucleic acid amplification device 1000 via the outlet ports of the sample module, and fluid (e.g., gas, liquid, or both) displaced from the nucleic acid amplification module flows via outlet ports 1016 and 1018 of the nucleic acid amplification module into the inlet ports of the sample module.

In more detail, the sample and buffer flow from the sample chamber of a receiver module to hydrate RPA reagents (e.g., dried oligomers) in the sample chamber of the transfer module, through the outlet port an into inlet port 1012. First pump 1040 advances this primary reaction mixture through first flow detection chamber 1042.

From the flow detection chamber, the primary reaction mixture is drawn into the first pump, through mixing chamber 1044, to second flow detection chamber 1046, and into primary reaction chamber 1020. Primary reaction chamber 1020 includes RPA reagent 1022 (e.g., $Mg^{2+}$ in the form of magnesium acetate) and is coupled to a heater and a mixer. The mixer may be present as magnetic mixer 1048. After a sufficient mixing time, first pump 1040 advances the product formed in primary reaction chamber 1020 to third flow detection chamber 1050. From third flow detection chamber 1050, air and a portion of the product of the primary RPA reaction from the primary reaction chamber flow toward the sample module via outlet port 1016.

An aliquot of the product from primary reaction chamber 1020 is pulled from shunt 1052 by second pump 1054 and flows toward fourth flow detection chamber 1056. Third pump 1058 pulls reagents (e.g., buffer) for the secondary RPA reaction from the blank chamber of the transfer module via the outlet port of the transfer module into inlet port 1014 of nucleic acid amplification device 1000 and through fifth flow detection chamber 1060. Fourth flow detection chamber 1056 and fifth flow detection chamber 1060 meet in a Y junction 1062, mixing selected amounts of the product from the first RPA reaction with reagents for the secondary RPA reaction. This mixture is pumped by second pump 1054 and third pump 1058 through a first series of mixing elements 1064 and a second series of mixing elements 1066. After passing through mixing elements 1066, the mixture is bifurcated at junction 1068 and bifurcated again at junction 1070 to yield four streams of the reaction mixture. Each stream flows through first reagent reservoir 1024 with mixing cylinders 1072 configured to mix the reaction mixture with reagent 1028 (e.g., $Mg^{2+}$ in the form of magnesium acetate). From first reagent reservoirs 1024, each mixture flows through second reagent reservoir 1026 containing reagent 1030. Reagent 1030 in second reagent reservoirs 1026 may be the same or different. In one example, at least two of reagents 1030 include different RPA primers for particular targets of interest, such as influenza A virus and influenza B virus.

From second reagent reservoirs 1026, third pump 1058 drives the mixtures through mixing elements 1074 and into secondary reaction chambers 1032. Secondary amplification occurs in secondary reaction chambers 1032. Secondary reaction chambers 1032 may also function as detection chambers. In nucleic acid amplification device 1000, secondary reaction chambers 1032 have an optically transparent covering, such that fluorescent signals generated when the fluorophore and quencher are separated via an exonuclease can be detected optically in an analyzer in which the nucleic acid amplification device is configured to be inserted, such as the analyzer described with respect to FIGS. 15-18.

Figure 12:
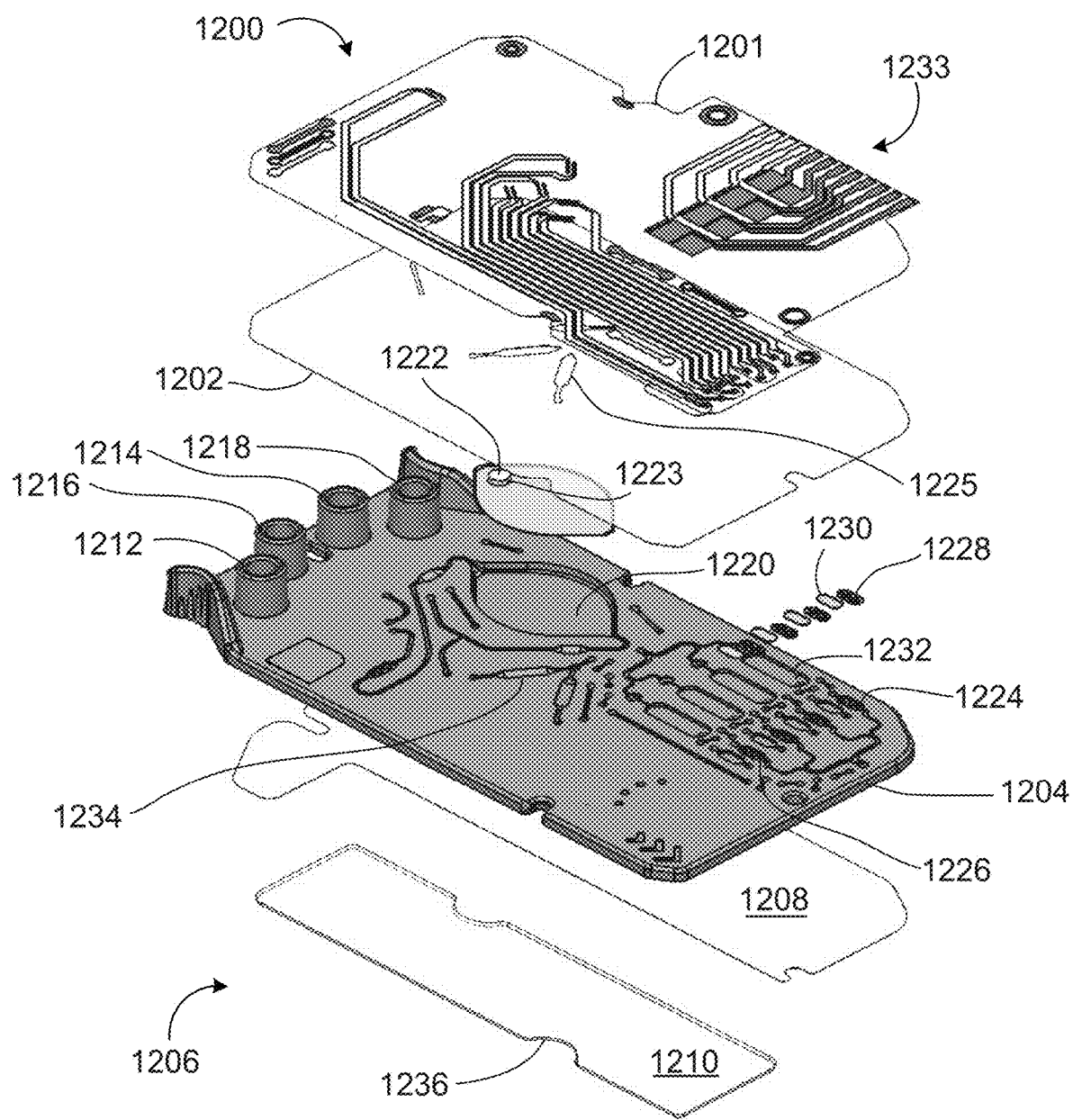
FIG. 12 depicts an exploded view of a microfluidic nucleic acid amplification device for detection of electrochemical probes.

FIG. 12 depicts an exploded view of nucleic acid amplification device 1200 for electrochemical detection. Nucleic acid amplification device 1200 is a laminated microfluidic device including sensor layer 1201, top layer 1202, intermediate layer 1204, and base layer 1006. Base layer 1206 may include more than one component. As depicted, base layer 1206 include two components 1208 and 1210.

Intermediate layer 1204 includes inlet ports 1212 and 1214 and outlet ports 1216 and 1218, which couple to outlet ports and inlet ports, respectively, of a sample module. Intermediate layer 1204 typically includes reagents, such as RPA reagents. As depicted in FIG. 12, primary reaction chamber 1220 includes a solid reagent 1222 (e.g., $Mg^{2+}$ in the form of magnesium acetate). A stirrer 1223 may be embedded in solid reagent 1222. In one example, the stirrer is a magnetic puck. Secondary reaction chambers 1232 may also function as detection chambers, with openings 1225 in top layer 1202 allowing liquid in the reaction chambers to contact electrodes 1233 on an underside of sensor layer 1201. Intermediate layer 1204 may also include flow detection chambers 1234, in which the presence of fluid is monitored electrically by electrodes in sensor layer 1201 superimposed over openings in top layer 1202, such that liquid flowing through the flow detection chambers contacts the electrodes. Registration features 1236 allow alignment of nucleic acid amplification device 1200 in an analyzer.

Nucleic acid amplification device 1200 may include additional features not depicted in FIG. 12, such as pumps and microfluidic pathways. One or more of the pumps may be a peristaltic pump or a syringe pump. The pumps may selectively drive reagents from the sample module and the primary reaction chamber 1220 toward secondary reaction chambers 1232 based on elapsed time or flow of fluid through flow detection chambers detected by sensors in an electrical analyzer, metering aliquots as needed.

Figure 13:
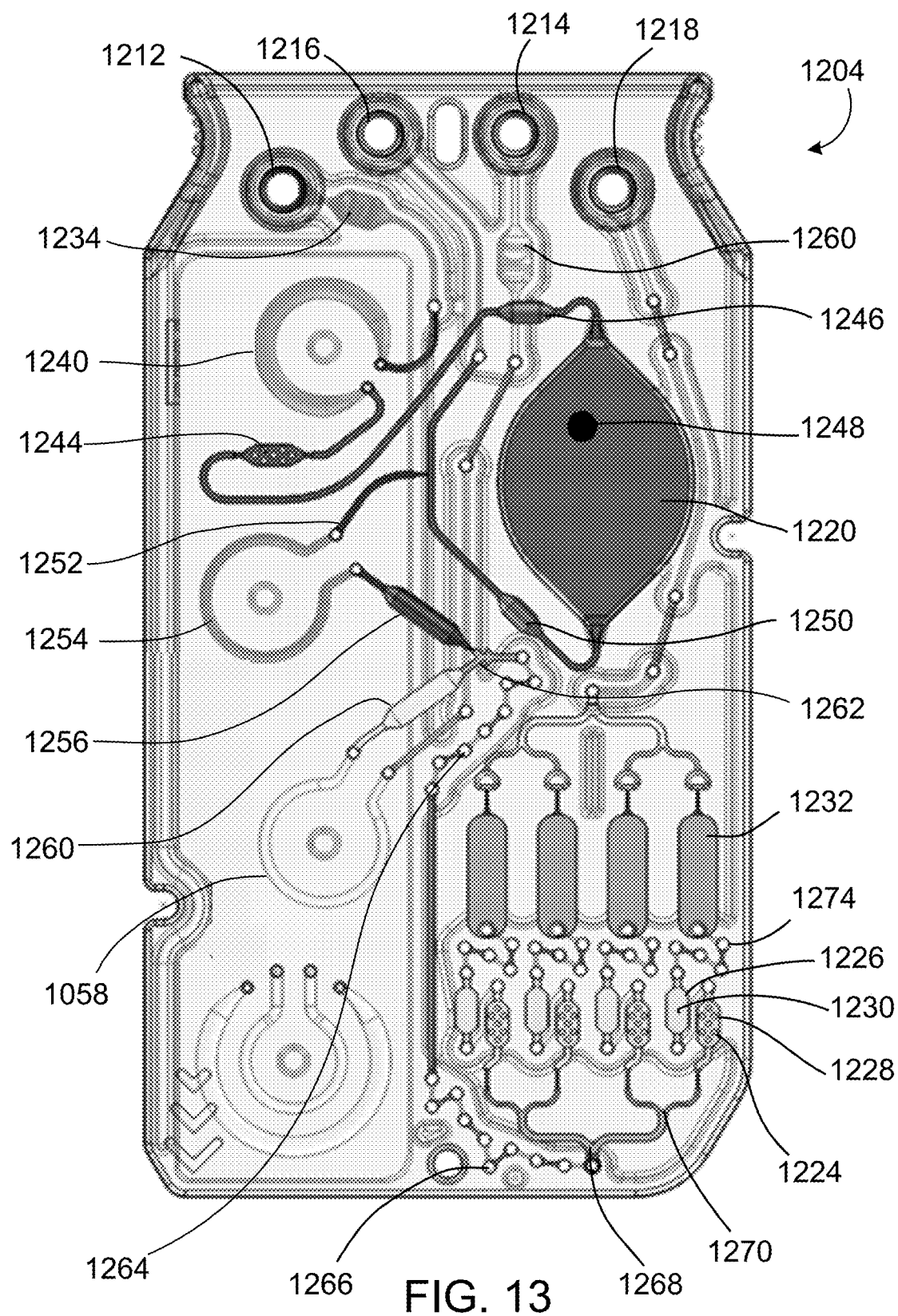
FIG. 13 depicts a top see-through view of intermediate layer of the microfluidic nucleic acid amplification device depicted in FIG. 12.

Operation of nucleic acid amplification device 1200 with a sample module is described with respect to FIG. 13, which depicts a top, see-through view of intermediate layer. When a sample module is coupled to nucleic acid amplification device 1200, outlet ports of the sample module are coupled to inlet ports 1212 and 1214 of the nucleic acid amplification device, and inlet ports of the sample module are coupled to outlet ports 1216 and 1218 of the nucleic acid amplification device. Reagents in the sample module flow into inlet ports 1212 and 1214 of nucleic acid amplification device 1200 via the outlet ports of the sample module, and fluid (e.g., gas, liquid, or both) displaced from the nucleic acid amplification module flows via outlet ports 1216 and 1218 of the nucleic acid amplification module into the inlet ports of the sample module.

In more detail, the sample and buffer flow from the sample chamber of a receiver module to hydrate RPA reagents (e.g., dried oligomers) in the sample chamber of the transfer module, through the outlet port an into inlet port 1212. First pump 1240 advances this primary reaction mixture through first flow detection chamber 1242 into the first pump, through mixing chamber 1244, to second flow detection chamber 1246, and into primary reaction chamber 1220. Primary reaction chamber 1220 includes RPA reagent 1222 (e.g., $Mg^{2+}$ in the form of magnesium acetate) and is coupled to a heater and a mixer. The mixer may be present as magnetic mixer 1248. After a sufficient mixing time, first pump 1240 advances the product formed in primary reaction chamber 1220 to third flow detection chamber 1250. From third flow detection chamber 1250, air and a portion of the product of the primary RPA reaction from the primary reaction chamber flow toward the sample module via outlet port 1216.

An aliquot of the product from primary reaction chamber 1220 is pulled from shunt 1252 by second pump 1254 and flows toward fourth flow detection chamber 1256. Third pump 1258 pulls reagents (e.g., buffer) for the secondary RPA reaction from the blank chamber of the transfer module via the outlet port of the transfer module into inlet port 1214 of nucleic acid amplification device 1200 and through fifth flow detection chamber 1260. Fourth flow detection chamber 1256 and fifth flow detection chamber 1260 meet in a Y junction 1262, mixing selected amounts of the product from the first RPA reaction with reagents for the secondary RPA reaction. This mixture is pumped by second pump 1254 and third pump 1258 through a first series of mixing elements 1264 and a second series of mixing elements 1266. After passing through mixing elements 1266, the mixture is bifurcated at junction 1268 and bifurcated again at junctions 1270 to yield four streams of the reaction mixture. Each stream flows through first reagent reservoir 1224 with mixing cylinders 1272 configured to mix the reaction mixture with reagent 1228 (e.g., $Mg^{2+}$ in the form of magnesium acetate). From first reagent reservoirs 1224, each mixture flows through second reagent reservoir 1226 containing reagent 1230. Reagent 1230 in second reagent reservoirs 1226 may be the same or different. In one example, at least two of reagents 1230 include different RPA primers for particular targets of interest, such as influenza A virus and influenza B virus.

From second reagent reservoirs 1226, third pump 1258 drives the mixtures through mixing elements 1274 and into secondary reaction chambers 1232. Secondary amplification occurs in secondary reaction chambers 1232. Secondary reaction chambers 1232 may also function as detection chambers. In nucleic acid amplification device 1200, liquid in secondary reaction chambers 1232 contacts electrodes on an underside of sensor layer 1201, such that electrons resulting from the oxidation of a redox active compound, such as described in U.S. Ser. No. 62/300,242, that has been cleaved from an RPA probe that is labelled with the redox active compound, are detected by the analyzer in which the nucleic acid amplification device is configured to be inserted.

Figure 14:
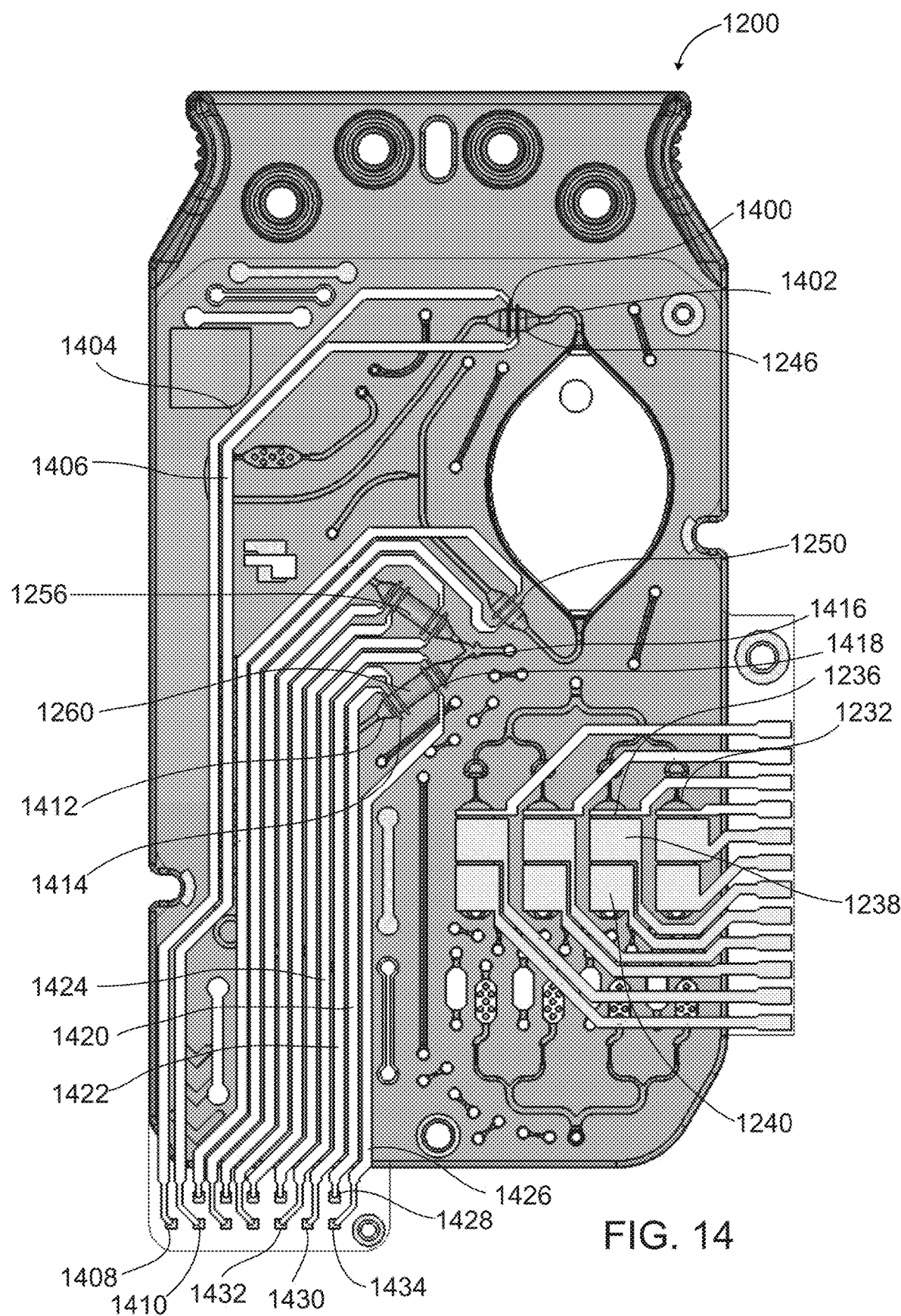
FIG. 14 depicts a top see-through view through sensor layer of the microfluidic nucleic acid amplification device depicted in FIG. 12.

FIG. 14 depicts a top, see-through view of nucleic acid amplification device 1200 with electrodes in sensor layer 1201 superimposed over openings in top layer 1202 and intermediate layer 1204. Electrodes are positioned on an underside of sensor layer 1201 to contact liquid in flow sensor detectors 1246, 1250, 1256, and 1260 and reaction chambers 1232. In one example, sensing electrodes, as well as conductive tracks, which electrically couple the sensing electrodes to terminals which electrically communicate with an analyzer may be formed by disposing a first conductive layer on sensor layer. In another example, the first conductive layer may be disposed over a second conductive layer on the sensor layer. The electrodes may be electrically isolated by masking the conductive layers and disposing a dielectric layer over the exposed regions. In one example, the first conductive material includes carbon. In another example, the second conductive material includes silver. As used herein, "disposing" includes printing methods, such as screen printing. When a silver layer is deposited beneath the carbon layer, the resulting conductive track typically has a lower resistance when compared with a conductive track formed using carbon alone. In both examples electrochemical measurements are performed on a carbon surface.

Flow sensor detectors 1246 and 1250 are each electrically coupled to two liquid sense electrodes. For flow sensor detector 1246, liquid sense electrodes 1400 and 1402 are electrically coupled to wirings 1404 and 1406, which are electrically coupled to connections 1408 and 1410, respectively. Flow sensor detectors 1256 and 1260 are each electrically coupled to four liquid sense electrodes. For flow sensor detector 1260, liquid sense electrodes 1412 and 1414 are electrically coupled to wirings 1420 and 1422, which are electrically coupled to connections 1428 and 1430, respectively, and electrodes 1416 and 1418 are electrically coupled to wirings 1424 and 1426, which are electrically coupled to connections 1432 and 1434, respectively. Each detection chamber 1232 is coupled to three measurement electrodes, including reference electrode 1436, working electrode 1438, and counter electrode 1440, and each electrode is electrically coupled to connections via wirings. The wirings may be conductive traces including a conductive material (e.g., silver). The connections are configured to engage terminals in an analyzer.

The liquid sense electrodes operate on principle of conductivity. That is, a voltage is applied across the terminals, and when fluid contacts the sense electrodes within the respective chambers, current passes through the liquid, and the analyzer detects a flow of current. For the measurement electrodes, a potential is applied between the counter electrode and the working electrode; the reference electrode acts to ensure the applied potential is as expected. When operated in an amperometric mode, a current flows proportional to the concentration of electroactive species in contact with the working electrode (effectively electrons received or donated depending on whether oxidation or reduction of the target species occurs at the specified potential). In the differential pulse voltammetry mode, the potential is swept from one voltage to another and the resulting current recorded giving rise to peaks and or troughs as a result of the oxidation or reduction of the electroactive species.

Figure 15:
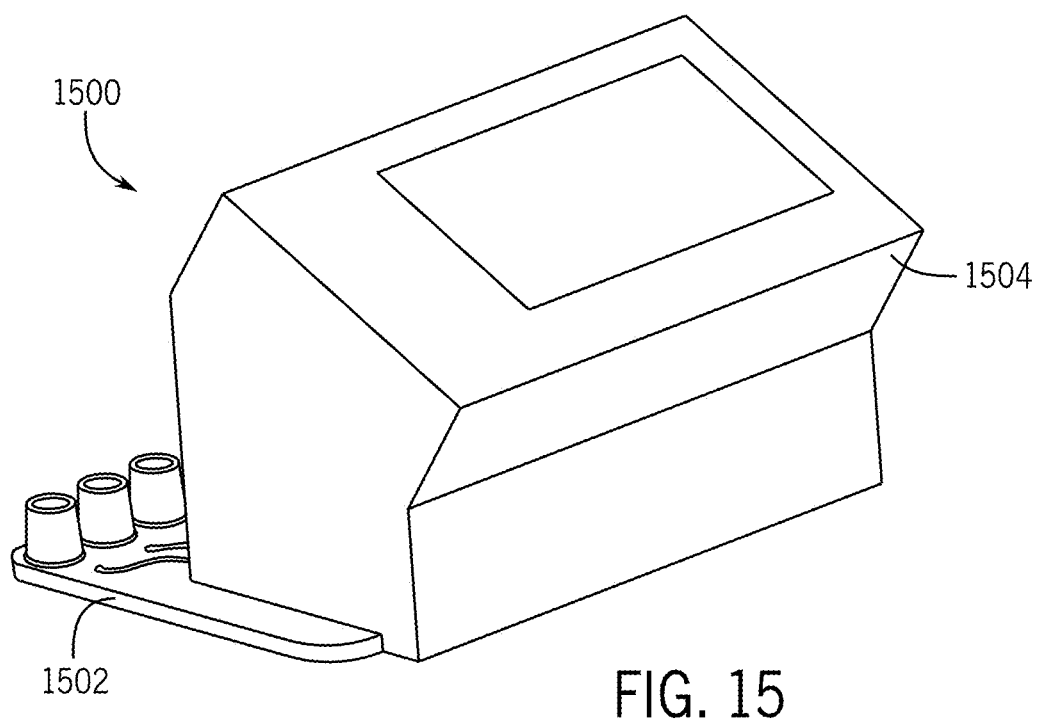
FIG. 15 depicts a perspective view of a nucleic acid amplification device inserted in an analyzer.

FIG. 15 depicts nucleic acid amplification system 1500, including nucleic acid amplification device 1502 inserted in analyzer 1504. Nucleic acid amplification device 1502 and analyzer may be configured for optical or electrochemical detection of RPA products. In some cases, insertion of nucleic acid amplification device in analyzer initiates assessment of the presence of target nucleic acid in a sample provided to the nucleic acid amplification device. In other cases, subsequent coupling of a sample module to nucleic acid amplification device initiates assessment of the presence of target nucleic acid in the sample. In still other cases, assessment of the presence of target nucleic acid in a sample provided to the nucleic acid amplification device is initiated by the user after insertion of the nucleic acid amplification device or assembly into the analyzer.

Figure 16:
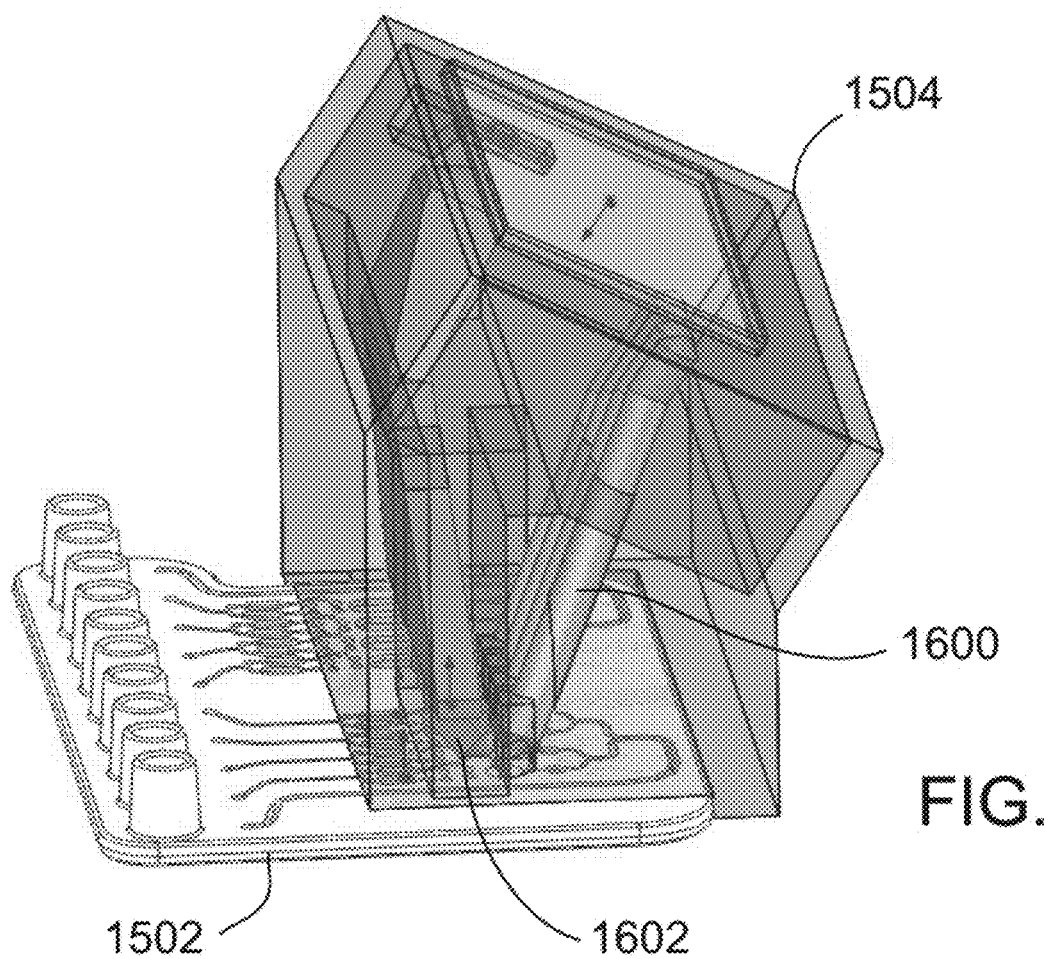
FIG. 16 depicts a see-through view of an optical analyzer.

As depicted in FIG. 16, nucleic acid amplification device 1502 and analyzer 1504 are configured for optical detection of RPA products. In particular, analyzer 1504 is configured to detect fluorescence from fluorescent probes coupled to RPA products in the detection chambers of nucleic acid amplification device 1502. Analyzer 1504 includes light sources, excitation light guides 1600 corresponding to each light source, emission light guides 1602 corresponding to each emission light guide, and a photodetector. The light sources are typically light emitting diodes (LEDs) selected to achieve a good match between the LED emission peak and absorption of the target fluorescent label. Analyzer 1504 incorporates a skew geometry to allow fluorescence measurement from multiple reaction cells using a single optical emission filter.

Figure 17:
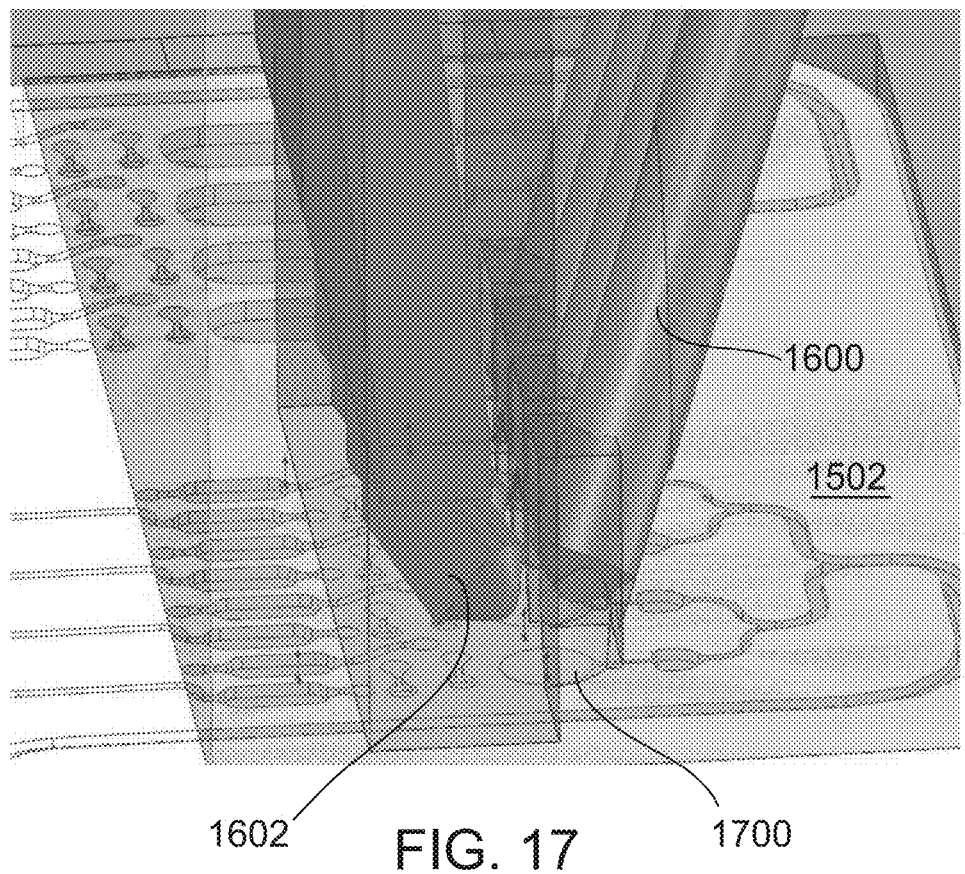
FIG. 17 depicts a detail view of light pipes in the optical analyzer depicted in FIG. 16.

FIG. 17 depicts an enlarged view of a portion of FIG. 16. As depicted in FIG. 17, analyzer 1504 includes four light sources to allow fluorescence measurement from four detection chambers 1700 in nucleic acid amplification device 1502. Excitation light guides 1600 direct light from the light sources to detection chambers 1700, and emission light guides 1602 direct the fluorescent emission from the detection chambers to a common photodiode via the optical filter. Discrimination is provided between the four measurement channels by time division multiplexing of the four light sources. Each excitation light guide 1600 is configured to direct incident light from one of the light sources to a target in a plane such that the angle between the incident light and the plane is in a range between 30° and 60° (e.g.,) 40°, and each emission light guide 1602 is configured to direct emitted light from the target to the photodetector such that an angle between the emitted light is between 40° and 60° (e.g.,) 30°. Analyzer 1504 typically includes a first lens and a second lens corresponding to each light source, with each corresponding excitation light guide configured to collimate light transmitted through the first lens from its corresponding light source and, via total internal reflection, direct the collimated light at an angle toward the second lens.

Figures 18A, 18B, 18C:
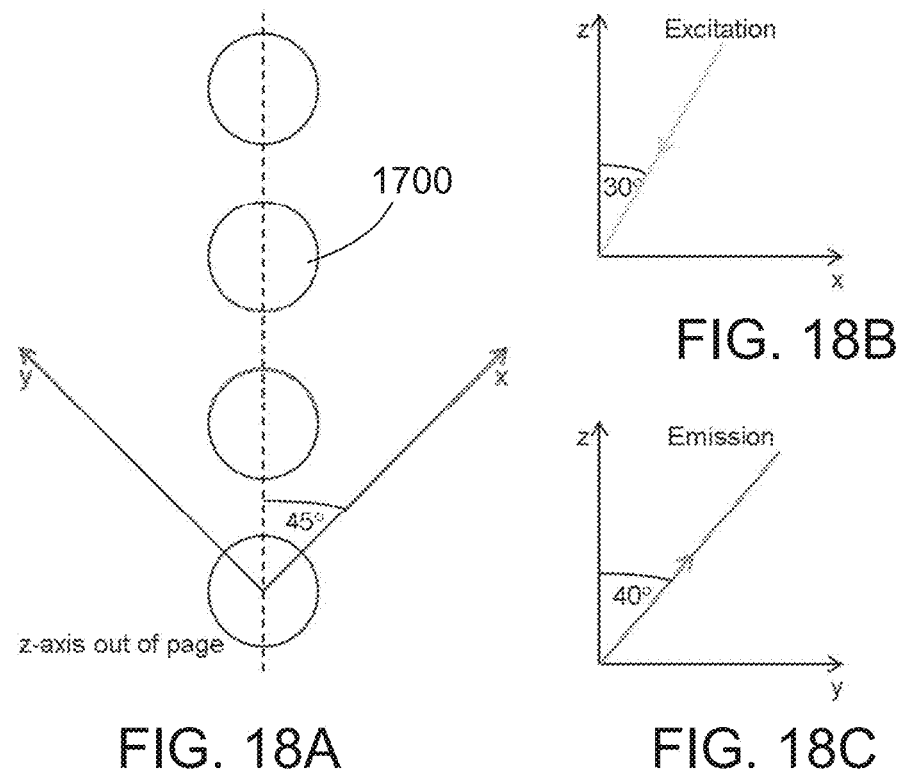
FIGS. 18A-18C depict excitation and emission coordinate systems described with respect to the optical analyzer depicted in FIG. 16.

FIGS. 18A-18C depict skew geometry of analyzer 1504. Angles depicted in FIGS. 18A-18C are exemplary and are selected for ease of explanation, however, these angles may be altered in embodiments of analyzer 1500. As depicted in FIG. 18A, the rotation axes are oriented at 45° to a line connecting the centers of reaction chambers 1700. This configuration facilitates avoiding positional clashes between the excitation light guides and the emission light guides. FIG. 18B depicts the excitation optical axis at 30° to the detection chamber surface normal (rotated in the x plane about they y axis). FIG. 18C depicts the emission optical axis at 40° to the detection chamber surface normal (about an orthogonal axis of rotation, i.e., rotated in the yz plane about the x axis). The center of rotation is below the normal liquid surface position (e.g., from 0.1 to 1 mm below). Other combinations of skew angles are listed in Table 1 below. A maximum bend angle in the excitation light guides and the emission light guides is typically 45° or less.

TABLE 1

Skew angles of excitation and emission light guides

| Emission light guide angle (°) | Excitation light guide angle (°) |
|---|---|
| 20 | 45 |
| 30 | 40 |
| 34 | 34 |
| 40 | 30 |
| 45 | 20 |

Analyzer 1504 includes a controller operatively coupled to the light sources and the photodetector. The controller initiates production of incident light by the light sources and initiates collection of emitted light from the detection chambers. Analyzer 1504 typically includes a single photodetector and a single emission filter operatively positioned between the emission light guides and the photodetector; however, in some embodiments, one or more additional photodetectors, emission filters, or both may be present.

While the devices and methods herein have been described as applications of Recombinase Polymerase Amplification (RPA) technology, other isothermal technologies for amplifying and detecting target nucleic acids may also be implemented in the devices described herein, for example Nicking and Extension Amplification Reaction (NEAR) technology. Methods of RPA amplification and detection of RPA amplification products, as described herein, are described in detail in U.S. Pat. Nos. 7,399,590; 8,580,507; 7,270,981; 7,399,590; 7,666,598; 7,435,561; 9,469,867; 9,057,097; 8,071,308; 8,637,253; and 8,062,850. NEAR methods are described in U.S. Patent Application Publication Nos. 2009/0081670 and 2009/0017453. Each of the foregoing references is incorporated herein by reference in its entirety and considered part of the present disclosure.

As described here, RPA employs enzymes, known as recombinases, which are capable of pairing oligonucleotide primers with homologous sequences in template double-stranded nucleic acid. RPA introduces a recombinase for inserting two primers with a template in duplex DNA, a single stranded DNA-binding protein for stabilizing the displaced strands of DNA and for preventing the primers from being displaced, and strand-displacing polymerase for extending primers bound to template DNA. In this way, DNA synthesis is directed to defined points in a template double-stranded nucleic acid. Using two or more sequence-specific (e.g., gene-specific) primers, an exponential amplification reaction is initiated if the template nucleic acid is present. The reaction progresses rapidly and results in specific amplification of a sequence present within the template double-stranded nucleic acid from just a few copies of the template nucleic acid to detectable levels of the amplified products within minutes. RPA processes proceed under isothermal conditions under physiological temperatures (e.g., 37-42° C.). RPA methods are disclosed, e.g., in U.S. Pat. Nos. 7,270,981; 7,399,590; 7,666,598; 7,435,561; US 2009/0029421; and WO 2010/141940, all of which are incorporated herein by reference.

RPA incorporates components of the cellular DNA replication and repair machinery, and establishes a 'dynamic' recombination environment having adequate rates of both recombinase loading and unloading that maintain high levels of recombination activity achieved in the presence of specific crowding agents. RPA has the advantage that it combines the sensitivity, specificity, and most other features of PCR, but without the need for thermocycling and with extraordinary speed and robustness to off-temperature setup. RPA benefits from the potential employment of a wide variety of nucleic acid processing enzymes such as known repair endonucleases which have been untapped by other processes due at least in part to the need for thermostable equivalents, poor regulation without accessory proteins such as single-stranded DNA binding proteins, or a combination thereof.

Briefly, RPA includes the following steps: first, a recombinase agent is contacted with a first and a second nucleic acid primer to form a first and a second nucleoprotein primer. Second, the first and second nucleoprotein primers are contacted with a double stranded target sequence to form a first double stranded structure at a first portion of the first strand and form a double stranded structure at a second portion of the second strand, so the 3' ends of said first nucleic acid primer and said second nucleic acid primer are oriented towards each other on a given template DNA molecule. Third, the 3' end of said first and second nucleoprotein primers are extended by DNA polymerases to generate first and second double stranded nucleic acids, and first and second displaced strands of nucleic acid. The second and third steps are repeated until a desired degree of amplification is reached.

This disclosure also provides for a method of performing nested RPA within a microfluidic cartridge or device. In a nested RPA, a first region of nucleic acid is amplified by RPA to form a first amplified region. Then a second region of nucleic acid that is completely within the first amplified region is amplified using RPA to form a second amplified region. This process may be repeated multiple times. For example, a third region of nucleic acid, which is completely within the second region, may be amplified from the second amplified region by RPA.

The RPA reagents disclosed herein can contain a set of primers that amplify the target nucleic acid sequence. The primers can include sequences that are complementary to the target nucleic acid sequence or that differ from the target nucleic acid sequence at one or more positions. As described herein, the amplification product of RPA with a primer that differs from the target nucleic acid sequence at one or more positions can differ from the target sequence at the one or more positions. The amplification product of the RPA reaction described herein can include a target cleavage sequence.

The set of RPA primers can amplify the target nucleic acid sequence or introduce a sequence that differs from the target nucleic acid sequence at one or more positions. This introduced sequence can consist of a target cleavage sequence. The first primer can be complementary to the target nucleic acid sequence. The second primer can include a first portion that is complementary to the target nucleic acid sequence and a second portion that is different from the target nucleic acid sequence at one or more positions. When the two primers amplify the nucleic acid sequence the second primer incorporates the one or more different positions into the amplified products. This amplified region is different from the target nucleic acid sequence at the one or more positions and can consist of the target cleavage sequence.

The RPA composition disclosed herein contains a recombinase, which may originate from prokaryotic, viral or eukaryotic origin. Exemplary recombinases include RecA and UvsX (e.g., a RecA protein or UvsX protein obtained from any species), and fragments or mutants thereof, and combinations thereof. The RecA and UvsX proteins can be obtained from any species. RecA and UvsX fragments or mutant proteins can also be produced using the available RecA and UvsS protein and nucleic acids sequences, and molecular biology techniques (see, e.g., the mutant forms of UvsX described in U.S. Pat. No. 8,071,308). Exemplary UvsX proteins include those derived from myoviridae phages, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, and phage LZ2. Additional exemplary recombinase proteins include archaebacterial RADA and RADB proteins and eukaryotic (e.g., plant, mammal, and fungal) Rad51 proteins (e.g., RAD51, RAD51B, RAD51C, RAD51D, DMC1, XRCC2, XRCC3, and recA) (see, e.g., Lin et al., Proc. Natl. Acad. Sci. U.S.A. 103:10328-10333, 2006).

In any process of this disclosure, the recombinase (e.g., UvsX) may be a mutant or hybrid recombinase. In some embodiments, the mutant UvsX is an Rb69 UvsX that includes at least one mutation in the Rb69 UvsX amino acid sequence, wherein the mutation is selected from the group consisting of (a) an amino acid which is not histidine at position 64, a serine at position 64, the addition of one or more glutamic acid residues at the C-terminus, the addition of one or more aspartic acid residues at the C-terminus, and a combination thereof. In other embodiments, the mutant UvsX is a T6 UvsX having at least one mutation in the T6 UvsX amino acid sequence, wherein the mutation is selected from the group consisting of: (a) an amino acid which is not histidine at position 66; (b) a serine at position 66; (c) the addition of one or more glutamic acid residues at the C-terminus; (d) the addition of one or more aspartic acid residues at the C-terminus; and (e) a combination thereof. Where a hybrid recombinase protein is used, the hybrid protein may, for example, be an UvsX protein that includes at least one region that includes an amino acid sequence derived from a different UvsX species. The region may be, for example, the DNA-binding loop-2 region of UvsX.

The DNA polymerase disclosed herein may be a eukaryotic or prokaryotic polymerase. Examples of eukaryotic polymerases include pol-alpha, pol-beta, pol-delta, pol-epsilon, and mutants or fragments thereof, or combinations thereof. Examples of prokaryotic polymerase include *E. coli* DNA polymerase I (e.g., Klenow fragment), bacteriophage T4 gp43 DNA polymerase, *Bacillus stearothermophilus* polymerase I large fragment, Phi-29 DNA polymerase, T7 DNA polymerase, *Bacillus subtilis* Pol I, *Staphylococcus aureus* Pol I, *E. coli* DNA polymerase I, *E. coli* DNA polymerase II, *E. coli* DNA polymerase III, *E. coli* DNA polymerase IV, *E. coli* DNA polymerase V, and mutants or fragments thereof, or combinations thereof. In some embodiments, the DNA polymerase lacks 3'-5' exonuclease activity. In some embodiments, the DNA polymerase has strand-displacing properties, e.g., large fragments of prokaryotic polymerases of class pol I or pol V.

Additionally, one or more single-stranded DNA binding proteins can be used to stabilize nucleic acids during the various exchange reactions that are ongoing in the reaction. The one or more single-stranded DNA binding proteins can be derived or obtained from any species, e.g., from a prokaryotic, viral or eukaryotic species. Non-limiting exemplary single-stranded DNA binding proteins include *E. coli* SSB and those derived from myoviridae phages, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, and phage LZ2. Additional examples of single-stranded DNA binding proteins include *A. denitrificans* Alide_2047, *Burkholderia thailandensis* BthaB_33951, *Prevotella pallens* HMPREF9144_0124, and eukaryotic single-stranded DNA binding protein replication protein A.

Any of the RPA processes of this disclosure may be performed in the presence of a crowding agent. In some embodiments, the crowding agent may include one or more of polyethylene glycol, polyethylene oxide, polyvinyl alcohol, polystyrene, Ficoll, dextran, poly(vinylpyrrolidone) (PVP), Triton-X, and albumin. In some embodiments, the crowding agent has a molecular weight of less than 200,000 daltons. In some embodiments of any of the aspects described here, the composition comprises a crowding agent selected from the group consisting of polyethylene glycol (PEG)(e.g., PEG1450, PEG3000, PEG8000, PEG10000, PEG14000, PEG15000, PEG20000, PEG250000, PEG30000, PEG35000, PEG40000, PEG compound with molecular weight between 15,000 and 20,000 daltons, or combinations thereof), dextran, polyvinyl alcohol, polyvinyl pyrrolidone, Triton-X, and Ficoll. In some embodiments, the crowding agent is present in the reaction mixture at a concentration between 1 to 15% by weight or by volume of the reaction mixture, e.g., between any two concentration values selected from 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0% 14.5% and 15.0%.

If a recombinase loading protein is used, the recombinase loading protein may be of prokaryotic, viral or eukaryotic origin. Exemplary recombinase loading proteins include *E. coli* RecO, *E. coli* RecR, UvsY, and mutants or fragments thereof, or combinations thereof. Exemplary UvsY proteins include those derived from myoviridae phages, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, and phage LZ2. In any of the processes of this disclosure, the recombinase loading agent may be derived from a myoviridae phage. The myoviridae phage may be, for example, T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, or phage LZ2.

Amplification methods suitable for use in the present methods include amplification methods performed without subjecting the polynucleotides to a temperature sufficient to denature double stranded polynucleotides during the amplification. For example, the amplification of the polynucleotides may be performed without subjecting the polynucleotides to a temperature in excess of about 90° C., about 80° C., about 70° C., or about 60° C. during amplification. In embodiments, the amplification of the polynucleotides is performed without subjecting the polynucleotides to conditions sufficient to denature double stranded polynucleotides during the amplification. For example, the amplification may be performed without subjecting the polynucleotides to physical, chemical, or thermal conditions sufficient to denature double stranded polynucleotides during amplification.

Amplification methods suitable for use in the present methods include amplification methods performed without first subjecting the polynucleotides to a temperature sufficient to denature double stranded polynucleotides present in the sample. For example, the amplification of the polynucleotides may be performed without first subjecting the polynucleotides to a temperature in excess of about 90° C., about 80° C., about 70° C., about 60° C., or about 55° C. In some embodiments, the polynucleotides and/or amplicons thereof are detected without first subjecting the polynucleotides to such excess temperatures. In some embodiments, the amplification of the polynucleotides is performed without first subjecting the polynucleotides to conditions sufficient to denature double stranded polynucleotides present in the sample. For example, the amplification may be performed without first subjecting the polynucleotides to physical, chemical, or thermal conditions sufficient to denature double stranded polynucleotides present in the sample.

Amplification methods suitable for use in the present methods include amplification methods performed in a total time (T) beginning with a step of combining the polynucleotides with reagents sufficient to perform the amplification and ending when amplification has proceeded by an amount sufficient to permit the qualitative or quantitative determination of the polynucleotides or amplicons thereof. In any of such embodiments, the total time T may be about 45 minutes or less, about 30 minutes or less, about 20 minutes or less, or about 15 minutes or less.

The amplification of the polynucleotides includes, for example, amplifying the polynucleotides by at least about $10^6$ fold, at least about $10^7$ fold, at least about $10^8$ fold, at least about $10^9$ fold, at least about $10^{10}$ fold, at least about $10^{11}$ fold, or at least about $10^{12}$ fold. Such amplification may be performed within the time T.

Amplification methods suitable for use in the present methods include "real time" or "quantitative" polynucleotide amplification methods known to the skilled artisan. Such methods detect the accumulation of polynucleotide amplification product after each amplification cycle in real time as the reaction progresses, allowing for the determination of amplification kinetics. Real time methods are quantitative because the time (e.g., number of cycles) to reach a specific threshold concentration of amplified products directly relates to the initial copy number of the target nucleotide. According to some embodiments, the amplification reaction is monitored by electrochemical detection using the oligonucleotide probes described herein.

EXAMPLES

Example 1: Nested RPA Amplification

FIGS. 19A-19D represent results of analyses conducted using the method of performing nested RPA on a microfluidic card as described herein. The results demonstrate the capability of the nested RPA assay to distinguish between samples with different known targets. Samples were obtained from a commercial supplier of influenza positive and influenza negative sample materials. A series of measurements were performed using a total of ninety samples: thirty samples were known positive for influenza A (Inf A), ten samples were known positive for influenza B (Inf B) and fifty samples were known to be free of influenza A or B (negative). Each sample was applied to a single assay device, and a measurement was obtained from each of the four detection chambers on the assay card.

In each of the experiments shown in FIGS. 19A-19D, detection of reaction products was performed using fluorescently labelled probes. Detection of RPA reagents with labelled probes is previously described and typically involves at least one probe with a detectable label for detection of amplified target, if present. A probe may include a fluor and a quencher, which are separated following cleavage by a nuclease when the probe hybridizes to a complementary polynucleotide sequence, if present in amplification reaction products. Similar results (not shown) were obtained with the ninety samples with respect to identification of whether a sample was influenza A positive, influenza B positive or a negative control, when the samples were tested using electrochemically labelled probes.

The combined results of both fluorescent and electrochemical probe measurements are depicted in Tables 2A-2D. Each Table includes comparative measurements made using a standard commercial qPCR assay that was performed by the supplier of the influenza sample materials. qPCR was performed at the point of sample acquisition by the commercial supplier of sample material, the results of which were used to classify the samples as positive or negative, as well as fluA or fluB; classified samples were stored suitably and were supplied in viral transport medium (VTM). There was no apparent influence of the VTM on the performance of RPA.

TABLE 2A

Fluorescence Detection of Influenza A Samples

| Inf A fluorescence | qPCR: positive | qPCR: negative | Predicative value |
|---|---|---|---|
| positive | 30 | 0 | PPV 100% (85.9-100) |
| negative | 0 | 60 | NPV 100% (92.5-100) |
| invalids | | | invalid rate |
| performance | Sensitivity 100% (85.9-100) | Specificity 100% (92.5-100) | Total 90 |

TABLE 2B

Fluorescence Detection of Influenza B Samples

| Inf B fluorescence | qPCR: positive | qPCR: negative | Predicative value |
|---|---|---|---|
| positive | 10 | 0 | PPV 100% (85.6-100) |
| negative | 0 | 80 | NPV 100% (94.3-100) |
| invalids | | | invalid rate |
| performance | Sensitivity 100% (85.9-100) | Specificity 100% (94.3-100) | Total 90 |

TABLE 2C

Electrochemical Detection of Influenza A Samples

| Inf A Echem | qPCR: positive | qPCR: negative | Predicative value |
|---|---|---|---|
| positive | 30 | 0 | PPV 100% (85.5-100) |
| negative | 0 | 59 | NPV 100% (92.4-100) |
| invalids | | 1 | invalid rate 3.33% |
| performance | Sensitivity 100% (85.9-100) | Specificity 100% (92.4-100) | Total 90 |

TABLE 2D

Electrochemical Detection of Influenza B Samples

| Inf B Echem | qPCR: positive | qPCR: negative | Predicative value |
|---|---|---|---|
| positive | 10 | 0 | PPV 100% (85.6-100) |
| negative | 0 | 79 | NPV 100% (94.2-100) |
| invalids | | 1 | Invalid rate |
| performance | Sensitivity 100% (55.5-100) | Specificity 100% (94.2-100) | Total 90 |

Because the nucleic acid sequence of influenza A is known to frequently change from year to year, the RPA assay was developed to incorporate two different primer and probe sets that were directed to different nucleotide regions to maximise the likelihood of identifying samples positive for influenza A.

The primers and probes used in the RPA assay as described herein are listed herein below as SEQ ID NOS. 1 to 21. During the first round of nested amplification the primary primer sequences were used to contact the whole sample in the first reaction chamber in order to perform primary amplification. The product of primary amplification was then used to contact the secondary primers and probes within the individual secondary reaction chambers to specifically amplify the respective target species using InfA PA, InfA PB2, InfB PA and IC to generate a signal whenever fluA or fluB is present in a patient sample. When probes were used for making fluorescence measurements, these were designed to be cleaved by the nuclease Exonuclease III (Exo); probes used for electrochemistry were designed for use with the nuclease 8-oxoguanine DNA glycosylase (fpg). Examples of suitable electrochemical probes are described in co-pending application PCT/US2017/019446, filed 24 Feb. 2017 and incorporated herein by reference in its entirety.

```
InfA[PA] primary amplification primers
>FluAPAR111
                                      (SEQ ID NO. 1)
TGCATGTGTGAGGAAGGAGTTGAACCAAG*A >FluAPAF523
                                      (SEQ ID NO. 2)
AAATTGCTTCTCATTGTTCAGGCACTTAGGG*A InfA[PB2] primary amplification primers
>FluAPB2F201
                                      (SEQ ID NO. 3)
GAACTGAGTAACCTTGCAAARGGGGAAAAGG*C >FluAPB2F218
                                      (SEQ ID NO. 4)
GAACTGAGTAACCTTGCAAAAGGGGAAAAAG*C >FluAPB2R103
                                      (SEQ ID NO. 5)
AYTAATTGATGGCCATCCGAATTCTTTTGGTCGCT*G InfB[PA] primary amplification primers
>FluBPAF44
                                      (SEQ ID NO. 6)
AAGGATTGGCTGATGATTACTTTTGGAAAAAGAAA*G >FluBPAR42
                                      (SEQ ID NO. 7)
TAATTCAGCCTGAAGTTCTGTGAGTCTGCTTAG*C Xcon primary amplification primers
>XConF7
                                      (SEQ ID NO. 8)
AATCATGAACCTCATGGCATCTTCCCTCGCCGC*C >XConR6
                                      (SEQ ID NO. 9)
ACAATGCAATCATATGCTTCTGCTATGTTAAGC*G InfA[PA] secondary amplification primers
>FLUPAF507ii
                                      (SEQ ID NO. 10)
AACCTGGGACCTTTGATCTTGGGGGGCTATAT*G >FLUAPAR106ii
                                      (SEQ ID NO. 11)
ATGTGTTAGGAAGGAGTTGAACCAAGAAGCAT*T
```

InfA[PA] Exo probe
>FluAPAExoP12dFAM F = dT-FAM, H = THF (abasic site mimic), Q = dT-BHQ-1, 3' = block C3spacer
(SEQ ID NO. 12)
GAACCAAGATGCATTRAGCAAAACCCAGGGAFHAQTAATCAGGCACTC InfA[PB2] secondary amplification primers
>FluAPB2F403
(SEQ ID NO. 13)
AATGTGCTAATYGGGCAAGGAGACGTGGTGTTG*G >FluAPB2R703
(SEQ ID NO. 14)
GGCCATCCGAATTCTTTTGGTCGCTGTCTGG*C InfA[PB2] Exo probe
>FluAPB2ExoP2 F = dT-FAM, H = THF (abasic site mimic), Q = dT-BHQ-1, 3' = block C3spacer
(SEQ ID NO. 15)
CGAATTCTTTTGGTCGCTGTCTGGCTGTCAGTAAGFHQGCTAGAGTCCCG InfB[PA] secondary amplification primers
>MSFBPA_F6 + 1-2
(SEQ ID NO. 16)
GGAAAAAGAAAGAAAAGCTGGGAAATAGCATG*G

>MSFBPA_R6 + 1
(SEQ ID NO. 17)
GCTTAGCACTCTCCCTTTCCCTTCCTCATCCAAT*G

InfB[PA] Exo probe
>MSFBPAx1 F = dT-FAM, H = THF (abasic site mimic), Q = dT-BHQ-1, 3' = block C3spacer
(SEQ ID NO. 18)
ACTGATGATATTCAGCTACAATCAAGACFAHQCGTTAAGTAATGAA Xcon secondary amplification primers
>XConR13
(SEQ ID NO. 19)
TTCCAGTCAGTCCTAGTCAGAAACGGTCCTTAGAC*G

>APOBEXTF
(SEQ ID NO. 20)
GCCAGGTTTATAGCACACTTGTCACCTA*C

Figure 19A:
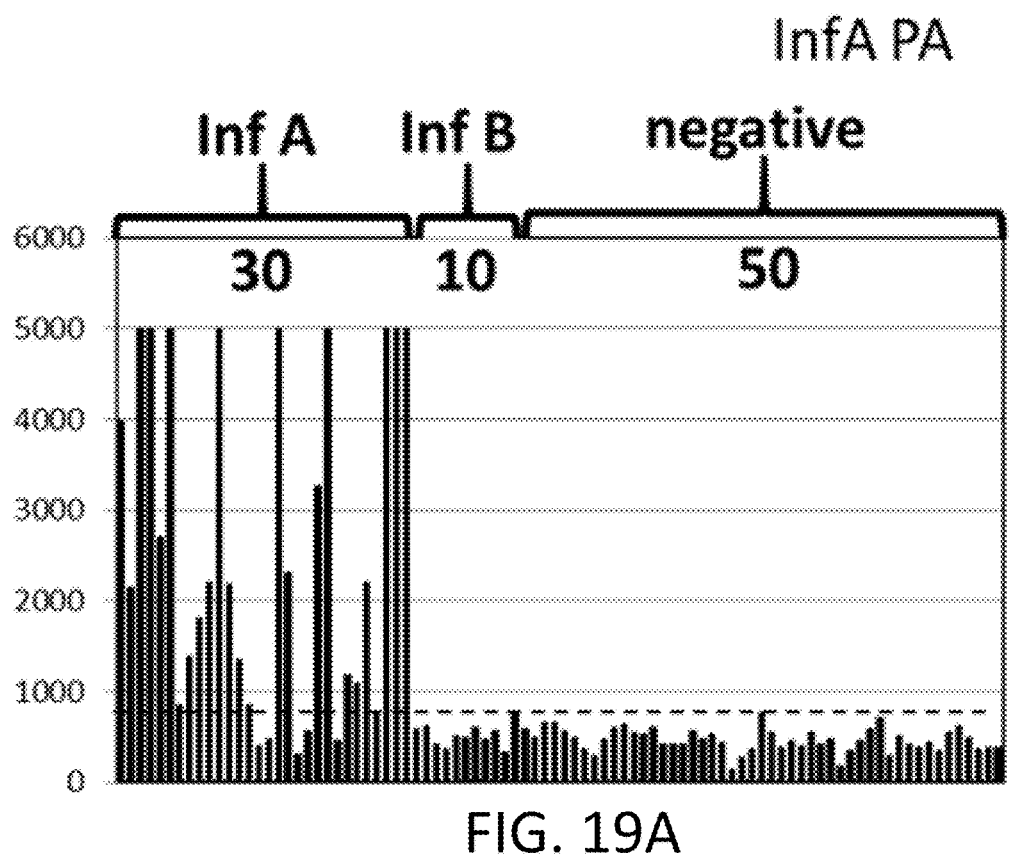
FIGS. 19A-19D depict the results of nested RPA amplification as described herein.
Figure 19B:
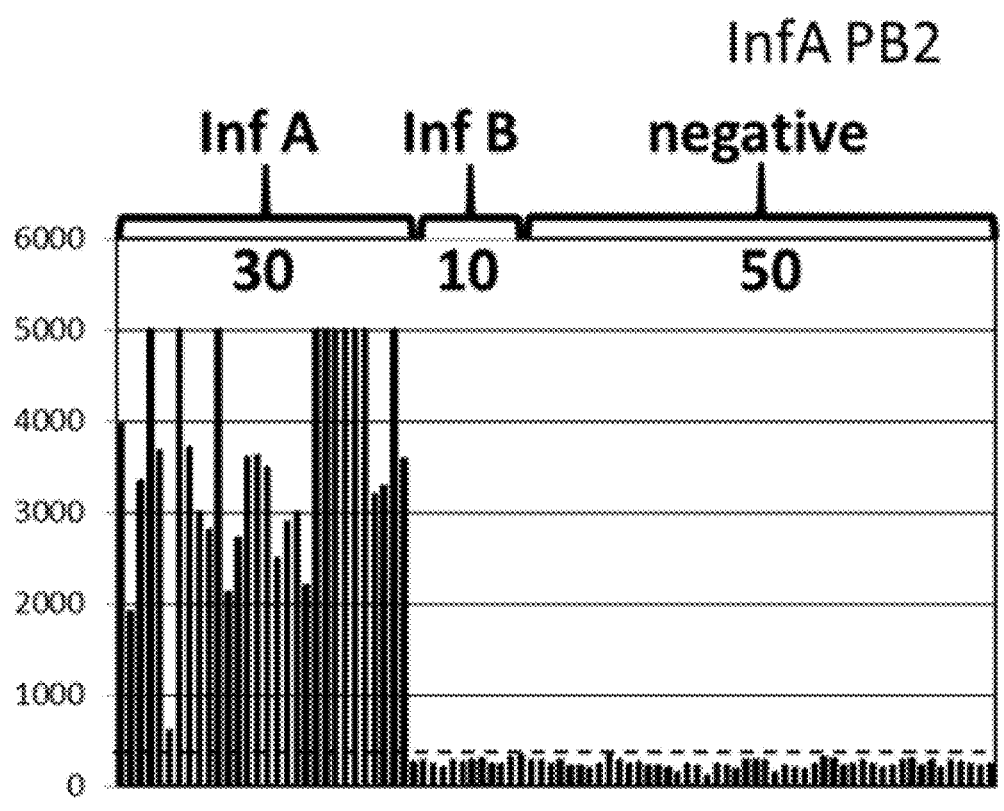
Figure 19C:
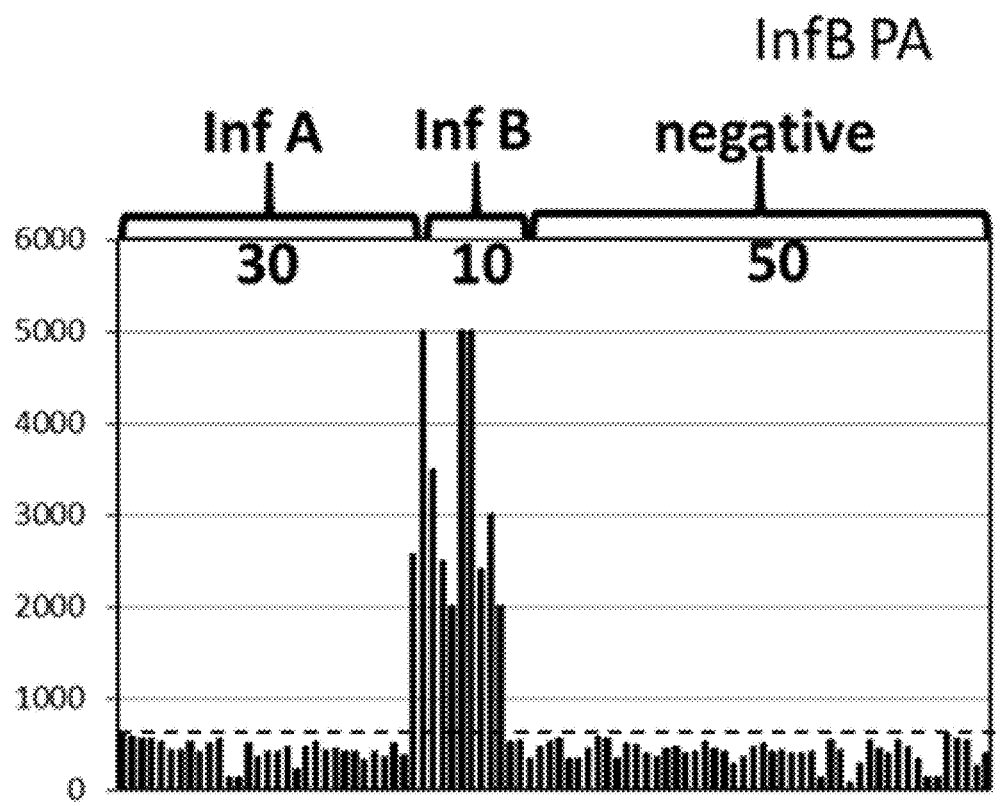
Figure 19D:
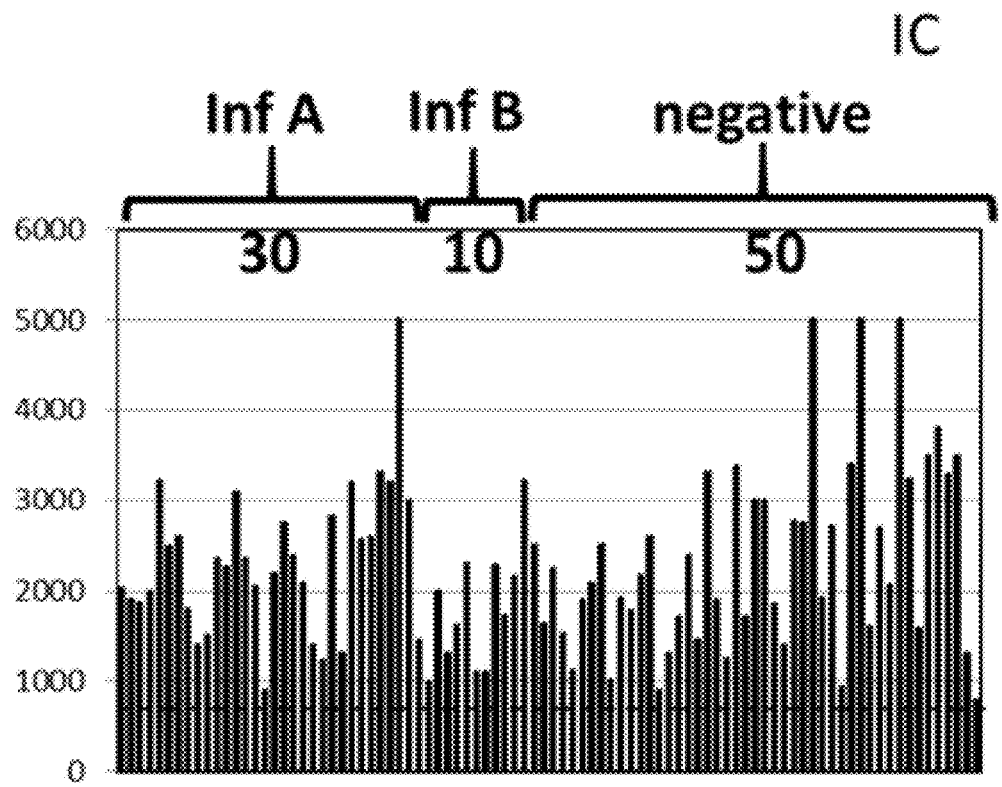

Xcon Exo probe
>APOB1FAM F = dT-FAM, H = THF (abasic site mimic), Q = dT-BHQ-1, 3' = block C3spacer
(SEQ ID NO. 21)
GCCAGGTTTATAGCACACTTGTCACCTACAQTHCFGATTGGTGGACTCT FIG. 19A represents the results obtained when the 90 samples were exposed to the InfA PA RPA primers and probes. The results indicate that the InfA PA primers detected 24 out of 30 InfA positive samples; none of the InfB or negative samples showed a response with the InfA PA primers. FIG. 19B shows that all of the InfA samples provided a positive response when exposed to InfA PB2 primers and probes; neither InfB nor negative samples showed any response with the InfA PB2 primers and probes. FIG. 19C shows that all of the InfB samples provided a positive response when exposed to the InfB PA primers and probes; neither the InfA nor negative control samples gave any response. FIG. 19D indicates when negative control primers (Xcon) and probes were used none of the samples showed a positive signal.

In each of FIGS. 19A-19D, the dashed line represents a baseline threshold, which was determined as three standard deviations above the maximum negative result. The data show that the combined use of RPA primers and probes against InfA PA and InfA PB2 regions resulted in a 100% identification of influenza A positive samples, demonstrating the ability of the assay format described herein to successfully determine the presence of influenza viruses with differing nucleotide sequences.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

---

What is claimed is:

1. A method comprising:
   providing the following as separate modules: 1) a microfluidic device comprising recombinase polymerase amplification reagents and a detection chamber comprising measurement electrodes; 2) a transfer module comprising oligomers; and 3) a receiver module comprising a sample;
   mating the transfer module and the receiver module to provide a sample module;
   mating the sample module to the microfluidic device;
   amplifying a target polynucleotide sequence in the sample, wherein the amplifying comprises:
      performing a first round of recombinase polymerase amplification on the sample to yield a first amplification product;
      moving a portion of the first amplification product to a secondary reaction chamber; and
      performing in the secondary reaction chamber a second round of recombinase polymerase amplification on the first amplification product to yield a second amplification product, wherein the second amplification product comprises a smaller sequence completely contained within the first amplification product produced during the first round of amplification;
   labeling the second amplification product with a first oligonucleotide probe linked to a redox moiety to yield a labeled second amplification product;
   cleaving the redox moiety from the labeled second amplification product; and
   electrochemically detecting a signal from the cleaved redox moiety with the measurement electrodes, wherein a detectable signal is indicative of the presence of the second amplification product.

2. The method of claim 1, wherein the redox moiety is selected from the group consisting of phenothiazine, a phenoxazine, a ferrocene, ferricyanide, ruthenium (III), osmium (II), an anthraquinone, a phenazine, and derivatives thereof.

3. The method of claim 1, wherein cleaving the redox moiety is performed using a nuclease.

4. The method of claim 3, wherein the nuclease targets double-stranded DNA.

5. The method of claim 4, wherein the nuclease is formamidopyrimine-DNA glycosylase.

6. The method of claim 1, wherein the sample is obtained from an animal.

7. The method of claim 6, wherein the sample obtained from an animal is obtained from the blood, sputum, mucus, saliva, tears, or urine of the animal.

8. The method of claim 6, wherein the sample is obtained from a human.

9. The method of claim 1, wherein a target nucleic acid comprises said target polynucleotide sequence and a sequence complementary to at least a portion of a primer sequence.

10. The method of claim 9, wherein the target nucleic acid is obtained from an animal pathogen.

11. The method of claim 10, wherein the animal pathogen is a single-stranded DNA virus, double-stranded DNA virus, or single-stranded RNA virus.

12. The method of claim 10, wherein the animal pathogen is a bacterium.

13. The method of claim 10, wherein the animal pathogen is an influenza A virus or an influenza B virus.

14. The method of claim 9, wherein the target nucleic acid is double-stranded DNA, single-stranded DNA, or RNA.

15. The method of claim 9, wherein the target nucleic acid is selected from the group consisting of genomic DNA, plasmid DNA, viral DNA, mitochondrial DNA, cDNA, synthetic double-stranded DNA and synthetic single-stranded DNA.

16. The method of claim 9, wherein the target nucleic acid is viral DNA or viral RNA.

17. The method of claim 1, wherein two or more target polynucleotide sequences in the sample are amplified.

18. The method of claim 17, wherein a target polynucleotide sequence comprising an influenza A gene sequence and a target polynucleotide sequence comprising an influenza B gene sequence are amplified.

19. The method of claim 1, wherein two or more second amplification products are detected.

20. The method of claim 19, wherein a second amplification product comprising an influenza A gene sequence and a second amplification product comprising an influenza B gene sequence are detected.

* * * * *